US009934670B2

(12) United States Patent
Hyland et al.

(10) Patent No.: US 9,934,670 B2
(45) Date of Patent: *Apr. 3, 2018

(54) INFRASTRUCTURE MONITORING SYSTEM AND METHOD

(71) Applicant: Mueller International, LLC, Atlanta, GA (US)

(72) Inventors: Gregory E. Hyland, Atlanta, GA (US); Robert Paul Keefe, Alpharetta, GA (US); Marietta Edmonds Zakas, Atlanta, GA (US); Clayton Robert Barker, III, Atlanta, GA (US)

(73) Assignee: Mueller International, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/928,725

(22) Filed: Oct. 30, 2015

(65) Prior Publication Data

US 2016/0049067 A1    Feb. 18, 2016

Related U.S. Application Data

(63) Continuation of application No. 12/606,957, filed on Oct. 27, 2009, now Pat. No. 9,202,362.
(Continued)

(51) Int. Cl.
*G08B 21/00* (2006.01)
*G01N 21/94* (2006.01)
(Continued)

(52) U.S. Cl.
CPC ............. *G08B 21/18* (2013.01); *G01N 21/94* (2013.01); *G01N 33/0075* (2013.01);
(Continued)

(58) Field of Classification Search
CPC .......... E03B 9/02; G01D 4/002; G01D 4/004; G01D 4/006; G01D 4/008; G01N 21/94;
(Continued)

(56) References Cited

U.S. PATENT DOCUMENTS

| 691,904 A | 1/1902 | Hallbergh |
| 1,165,429 A | 12/1915 | Mass |

(Continued)

FOREIGN PATENT DOCUMENTS

| AU | 2009308949 | 5/2010 |
| AU | 2010249499 | 5/2015 |

(Continued)

OTHER PUBLICATIONS

Keyghobad, Seyamak; Notice of Allowance for U.S. Appl. No. 13/590,954, filed Aug. 21, 2012, dated Jul. 9, 2013, 21 pgs.
(Continued)

*Primary Examiner* — Quan-Zhen Wang
*Assistant Examiner* — Stephen Burgdorf
(74) *Attorney, Agent, or Firm* — Taylor English Duma LLP

(57) ABSTRACT

An infrastructure monitoring system includes: a first monitoring device configured to detect and monitor a first condition of a first aspect of the infrastructure and transmit a data signal including data relating to the first condition; a second monitoring device configured to detect and monitor a second condition of a second aspect of the infrastructure and transmit a data signal including data relating to the second condition; a third monitoring device configured to detect and monitor a third condition of a third aspect of the infrastructure and transmit a data signal including data relating to the third condition; and an operations center communicatively coupled to each monitoring device, the operations center configured to receive the data signal from
(Continued)

each monitoring device and determine whether the data included in the data signal received from any one of the monitoring devices indicates a problem within the infrastructure.

18 Claims, 1 Drawing Sheet

Related U.S. Application Data

(60) Provisional application No. 61/108,770, filed on Oct. 27, 2008, provisional application No. 61/180,600, filed on May 22, 2009.

(51) Int. Cl.
| G01N 33/00 | (2006.01) |
| G08B 25/08 | (2006.01) |
| G08B 21/18 | (2006.01) |
| H04M 11/04 | (2006.01) |
| G08B 25/00 | (2006.01) |
| G06F 15/00 | (2006.01) |

(52) U.S. Cl.
CPC ........... *G08B 25/009* (2013.01); *G08B 25/08* (2013.01); *H04M 11/04* (2013.01)

(58) Field of Classification Search
CPC .... G01N 33/0075; G06Q 10/08; G06Q 50/06; G08B 1/08; G08B 15/02; G08B 21/10; G08B 21/18; G08B 21/182; G08B 21/20; G08B 25/009; G08B 25/08; G08B 25/10; G08B 25/20; H04M 11/04; H04Q 9/00; H04Q 2209/00; Y02B 90/242; Y02B 90/243; Y02B 90/246; Y02B 90/247; Y04S 20/322; Y04S 20/42
USPC ................. 340/517, 539.22, 539.26, 870.02; 702/188
See application file for complete search history.

(56) References Cited

U.S. PATENT DOCUMENTS

| 1,788,618 A | 1/1931 | Cover |
| 1,808,209 A | 6/1931 | Earl |
| 1,808,212 A | 6/1931 | Earl |
| 2,302,529 A | 11/1942 | Cornell et al. |
| 3,254,660 A | 6/1966 | Ray |
| 3,593,957 A | 7/1971 | Dolter et al. |
| 3,653,261 A | 4/1972 | Feldman |
| 3,672,233 A | 6/1972 | Hjermstad |
| 3,705,385 A | 12/1972 | Batz |
| 3,731,534 A | 5/1973 | Painley et al. |
| 3,795,144 A | 3/1974 | Marchesi |
| 4,093,997 A | 6/1978 | Germer |
| 4,120,031 A | 10/1978 | Kincheloe et al. |
| 4,126,338 A | 11/1978 | Coel |
| 4,282,413 A | 8/1981 | Simons |
| 4,291,375 A | 9/1981 | Wolf |
| 4,388,690 A | 6/1983 | Lumsden |
| 4,414,633 A | 11/1983 | Churchill |
| 4,442,492 A | 4/1984 | Karlsson et al. |
| 4,465,970 A | 8/1984 | Dimassimo et al. |
| 4,516,213 A | 5/1985 | Gidden |
| 4,542,469 A | 9/1985 | Brandberry et al. |
| 4,591,988 A | 5/1986 | Klima et al. |
| 4,705,060 A | 11/1987 | Goulbourne |
| 4,707,852 A | 11/1987 | Jahr et al. |
| 4,727,900 A | 3/1988 | Dooling et al. |
| 4,778,204 A | 10/1988 | Berger |
| 4,792,946 A | 12/1988 | Mayo |
| 4,803,632 A | 2/1989 | Frew et al. |
| 4,833,618 A | 5/1989 | Verma et al. |
| 4,868,566 A | 9/1989 | Strobel et al. |
| 4,881,070 A | 11/1989 | Burrowes et al. |
| 4,901,751 A | 2/1990 | Story |
| 4,940,976 A | 7/1990 | Gastouniotis et al. |
| 4,945,344 A | 7/1990 | Farrell |
| 4,953,403 A | 9/1990 | Springer |
| 4,967,996 A | 11/1990 | Sonoda et al. |
| 4,989,830 A | 2/1991 | Ratnik |
| 5,056,107 A | 10/1991 | Johnson et al. |
| 5,075,792 A | 12/1991 | Brown et al. |
| 5,079,715 A | 1/1992 | Venkataraman et al. |
| 5,121,344 A | 6/1992 | Laage et al. |
| 5,239,575 A | 8/1993 | White et al. |
| 5,251,480 A | 10/1993 | Brunson, IV et al. |
| 5,261,275 A | 11/1993 | Davis |
| 5,267,587 A | 12/1993 | Brown |
| 5,298,894 A | 3/1994 | Cerny et al. |
| 5,327,925 A | 7/1994 | Ortel |
| 5,381,136 A | 1/1995 | Powers et al. |
| 5,434,911 A | 7/1995 | Gray et al. |
| 5,437,481 A | 8/1995 | Spears et al. |
| 5,438,329 A | 8/1995 | Gastounioulis et al. |
| 5,451,938 A | 9/1995 | Brennan, Jr. |
| 5,459,459 A | 10/1995 | Lee |
| 5,481,259 A | 1/1996 | Bane |
| 5,493,287 A | 2/1996 | Bane |
| 5,509,567 A | 4/1996 | Lindahl |
| 5,519,387 A | 5/1996 | Besier et al. |
| 5,525,898 A | 6/1996 | Lee et al. |
| 5,553,094 A | 9/1996 | Johnson et al. |
| 5,588,462 A | 12/1996 | McHugh |
| 5,590,179 A | 12/1996 | Shincovich et al. |
| 5,594,740 A | 1/1997 | Ladue |
| 5,594,776 A | 1/1997 | Dent |
| 5,617,084 A | 4/1997 | Sears |
| 5,631,554 A | 5/1997 | Briese et al. |
| 5,646,863 A | 7/1997 | Morton |
| 5,654,692 A | 8/1997 | Baxter, Jr. et al. |
| 5,655,299 A | 8/1997 | Lindahl |
| 5,666,655 A | 9/1997 | Ishikawa et al. |
| 5,673,252 A | 9/1997 | Johnson et al. |
| 5,708,195 A | 1/1998 | Kurisu et al. |
| 5,714,931 A | 2/1998 | Petite |
| 5,746,344 A | 5/1998 | Syler et al. |
| 5,748,104 A | 5/1998 | Argyroudis et al. |
| 5,751,797 A | 5/1998 | Saadeh |
| 5,754,101 A | 5/1998 | Tsunetomi et al. |
| 5,767,790 A | 6/1998 | Jovellana |
| 5,787,358 A | 7/1998 | Takahashi |
| 5,801,643 A | 9/1998 | Williams et al. |
| 5,815,086 A | 9/1998 | Ivie et al. |
| 5,852,658 A | 12/1998 | Knight et al. |
| 5,877,703 A | 3/1999 | Bloss et al. |
| 5,892,441 A | 4/1999 | Woolley et al. |
| 5,892,758 A | 4/1999 | Argyroudis |
| 5,907,491 A | 5/1999 | Canada et al. |
| 5,924,051 A | 7/1999 | Provost et al. |
| 5,926,103 A | 7/1999 | Petite |
| 5,926,531 A | 7/1999 | Petite |
| 5,940,009 A | 8/1999 | Loy et al. |
| 5,963,146 A | 10/1999 | Johnson et al. |
| 5,963,557 A | 10/1999 | Eng |
| 5,971,011 A | 10/1999 | Price |
| 5,979,863 A | 11/1999 | Lousberg |
| 5,986,573 A | 11/1999 | Franklin et al. |
| 5,993,739 A | 11/1999 | Lyon |
| 5,994,892 A | 11/1999 | Turino et al. |
| 5,996,608 A | 12/1999 | Hunter |
| 6,006,212 A | 12/1999 | Schleich et al. |
| 6,028,522 A | 2/2000 | Petite |
| 6,028,855 A | 2/2000 | Hirsch |
| 6,031,455 A | 2/2000 | Grube et al. |
| 6,031,466 A | 2/2000 | Leshets et al. |
| 6,044,062 A | 3/2000 | Brownrigg et al. |
| 6,058,374 A | 5/2000 | Guthrie et al. |
| 6,060,994 A | 5/2000 | Chen |
| 6,069,571 A | 5/2000 | Tell |
| 6,078,269 A | 6/2000 | Markwell |

(56) References Cited

U.S. PATENT DOCUMENTS

| | | |
|---|---|---|
| 6,081,204 A | 6/2000 | Lavoie et al. |
| 6,115,677 A | 9/2000 | Perthold et al. |
| 6,150,955 A | 11/2000 | Tracy et al. |
| 6,152,173 A | 11/2000 | Makowan |
| 6,163,276 A | 12/2000 | Irving et al. |
| 6,172,616 B1 | 1/2001 | Johnson et al. |
| 6,178,816 B1 | 1/2001 | Katzman et al. |
| 6,194,902 B1 * | 2/2001 | Kuo .................. G01N 17/00 324/535 |
| 6,195,018 B1 | 2/2001 | Ragle et al. |
| 6,208,266 B1 | 3/2001 | Lyons et al. |
| 6,218,953 B1 | 4/2001 | Petite |
| 6,233,327 B1 | 5/2001 | Petite |
| 6,246,677 B1 | 6/2001 | Nap et al. |
| 6,249,516 B1 | 6/2001 | Brownrigg et al. |
| 6,288,641 B1 | 9/2001 | Casais |
| 6,317,051 B1 | 11/2001 | Cohen |
| 6,333,975 B1 | 12/2001 | Brunn et al. |
| 6,373,399 B1 | 4/2002 | Johnson et al. |
| 6,392,538 B1 | 5/2002 | Shere |
| 6,405,047 B1 | 6/2002 | Moon |
| 6,424,270 B1 | 7/2002 | Ali |
| 6,426,027 B1 | 7/2002 | Scarborough et al. |
| 6,430,268 B1 | 8/2002 | Petite |
| 6,437,692 B1 | 8/2002 | Petite et al. |
| 6,453,247 B1 | 9/2002 | Hunaidi |
| 6,456,197 B1 | 9/2002 | Lauritsen et al. |
| 6,470,903 B2 | 10/2002 | Reyman |
| 6,493,377 B2 | 12/2002 | Schilling et al. |
| 6,512,463 B1 | 1/2003 | Campbell et al. |
| 6,528,957 B1 | 3/2003 | Luchaco |
| 6,536,469 B2 | 3/2003 | Dilger et al. |
| 6,538,577 B1 | 3/2003 | Ehrke et al. |
| 6,560,543 B2 | 5/2003 | Wolfe et al. |
| 6,564,159 B1 | 5/2003 | Lavoie et al. |
| 6,568,416 B2 | 5/2003 | Tucker |
| 6,577,961 B1 | 6/2003 | Hubbard et al. |
| 6,581,458 B1 | 6/2003 | Hathaway et al. |
| 6,618,578 B1 | 9/2003 | Petite |
| 6,618,709 B1 | 9/2003 | Sneeringer |
| 6,624,750 B1 | 9/2003 | Marman et al. |
| 6,628,207 B1 | 9/2003 | Hemminger et al. |
| 6,628,764 B1 | 9/2003 | Petite |
| 6,633,781 B1 | 10/2003 | Lee et al. |
| 6,653,945 B2 | 11/2003 | Johnson et al. |
| 6,657,552 B2 | 12/2003 | Belski et al. |
| 6,675,071 B1 | 1/2004 | Griffin, Jr. et al. |
| 6,675,834 B1 | 1/2004 | Lai |
| 6,677,861 B1 | 1/2004 | Henry et al. |
| 6,701,956 B1 | 3/2004 | Berger |
| 6,710,721 B1 | 3/2004 | Holowick |
| 6,747,557 B1 | 6/2004 | Petite et al. |
| 6,798,352 B2 | 9/2004 | Holowick |
| 6,816,072 B2 | 11/2004 | Zoratti |
| 6,836,737 B2 | 12/2004 | Petite et al. |
| 6,847,300 B2 | 1/2005 | Yee et al. |
| 6,848,303 B2 | 2/2005 | Oeder et al. |
| 6,880,567 B2 | 4/2005 | Klaver |
| 6,891,838 B1 | 5/2005 | Petite et al. |
| 6,912,472 B2 | 6/2005 | Mizushina et al. |
| 6,914,533 B2 | 7/2005 | Petite |
| 6,914,893 B2 | 7/2005 | Petite |
| 6,931,445 B2 | 8/2005 | Davis |
| 6,946,972 B2 | 9/2005 | Mueller et al. |
| 6,952,970 B1 | 10/2005 | Furmidge |
| 6,954,701 B2 | 10/2005 | Wolfe |
| 6,954,814 B1 | 10/2005 | Leach |
| 6,972,677 B2 | 12/2005 | Coulthard |
| 6,978,210 B1 | 12/2005 | Suter et al. |
| 6,980,079 B1 | 12/2005 | Shintani et al. |
| 6,982,651 B2 | 1/2006 | Fischer |
| 7,008,239 B1 | 3/2006 | Ju |
| 7,009,530 B2 | 3/2006 | Zigdon et al. |
| 7,012,546 B1 | 3/2006 | Zigdon et al. |
| 7,020,701 B1 * | 3/2006 | Gelvin .................. G01D 21/00 250/332 |
| 7,042,368 B2 | 5/2006 | Patterson et al. |
| 7,053,767 B2 | 5/2006 | Petite et al. |
| 7,054,271 B2 | 5/2006 | Brownrigg |
| 7,061,924 B1 | 6/2006 | Durrant et al. |
| 7,072,945 B1 | 7/2006 | Nieminen et al. |
| 7,079,810 B2 | 7/2006 | Petite et al. |
| 7,088,239 B2 | 8/2006 | Basinger et al. |
| 7,089,125 B2 | 8/2006 | Sonderegger |
| 7,099,781 B1 | 8/2006 | Heidl et al. |
| 7,103,511 B2 | 9/2006 | Petite |
| 7,111,817 B2 | 9/2006 | Teti et al. |
| 7,117,051 B2 | 10/2006 | Landry et al. |
| 7,123,628 B1 | 10/2006 | Hwang |
| 7,124,184 B2 | 10/2006 | Chung et al. |
| 7,137,550 B1 | 11/2006 | Petite |
| 7,142,107 B2 | 11/2006 | Kates |
| 7,143,645 B2 | 12/2006 | Benson et al. |
| 7,228,726 B2 | 6/2007 | Kates |
| 7,248,179 B2 | 7/2007 | Smit |
| 7,248,181 B2 | 7/2007 | Patterson et al. |
| 7,250,874 B2 | 7/2007 | Mueller et al. |
| 7,256,704 B2 | 8/2007 | Yoon et al. |
| 7,263,073 B2 | 8/2007 | Petite et al. |
| 7,267,014 B2 | 9/2007 | Winter |
| 7,272,635 B1 | 9/2007 | Longtin et al. |
| 7,292,143 B2 | 11/2007 | Drake et al. |
| 7,295,128 B2 | 11/2007 | Petite |
| 7,301,456 B2 | 11/2007 | Han |
| 7,304,587 B2 | 12/2007 | Boaz |
| 7,315,257 B2 | 1/2008 | Patterson et al. |
| 7,342,504 B2 | 3/2008 | Crane et al. |
| 7,346,030 B2 | 3/2008 | Cornwall |
| 7,349,766 B2 | 3/2008 | Rodgers |
| 7,353,280 B2 | 4/2008 | Chiles et al. |
| 7,356,614 B2 | 4/2008 | Kim et al. |
| 7,363,031 B1 | 4/2008 | Aisa |
| 7,385,524 B1 | 6/2008 | Orlosky |
| 7,397,907 B2 | 7/2008 | Petite |
| 7,412,882 B2 | 8/2008 | Lazar et al. |
| 7,417,557 B2 | 8/2008 | Osterloh et al. |
| 7,423,985 B1 | 9/2008 | Hill |
| 7,424,527 B2 | 9/2008 | Petite |
| 7,443,313 B2 | 10/2008 | Davis et al. |
| 7,444,401 B1 | 10/2008 | Keyghobad et al. |
| 7,453,373 B2 | 11/2008 | Cumeralto et al. |
| D583,692 S | 12/2008 | Ball et al. |
| 7,468,661 B2 | 12/2008 | Petite et al. |
| 7,478,108 B2 | 1/2009 | Townsend et al. |
| 7,480,501 B2 | 1/2009 | Petite |
| 7,526,539 B1 | 4/2009 | Hsu |
| 7,533,693 B2 | 5/2009 | Colton et al. |
| 7,549,439 B2 | 6/2009 | Kimura et al. |
| 7,550,746 B2 | 6/2009 | Tokhtuev et al. |
| 7,604,216 B2 | 10/2009 | Gebler |
| 7,650,425 B2 | 1/2010 | Davis |
| 7,671,480 B2 | 3/2010 | Pitchford et al. |
| 7,690,393 B2 | 4/2010 | Nagle et al. |
| 7,694,934 B2 | 4/2010 | Irwin |
| 7,696,940 B1 | 4/2010 | MacDonald |
| 7,697,492 B2 | 4/2010 | Petite |
| 7,739,378 B2 | 6/2010 | Petite |
| 7,740,024 B2 | 6/2010 | Brodeur |
| 7,746,246 B2 | 6/2010 | Salser |
| 7,752,309 B2 | 7/2010 | Keyghobad et al. |
| 7,756,086 B2 | 7/2010 | Petite |
| 7,760,703 B2 | 7/2010 | Kubler et al. |
| 7,775,422 B2 | 8/2010 | Winter et al. |
| 7,783,738 B2 | 8/2010 | Keyghobad et al. |
| 7,792,946 B2 | 9/2010 | Keyghobad et al. |
| 7,806,382 B2 | 10/2010 | Palumbo et al. |
| 7,817,063 B2 | 10/2010 | Hawkins et al. |
| 7,825,793 B1 | 11/2010 | Spillman et al. |
| 7,843,379 B2 | 11/2010 | Menzer et al. |
| 7,854,165 B2 | 12/2010 | Ball |
| 7,870,080 B2 | 1/2011 | Budike, Jr. |
| 7,880,641 B2 | 2/2011 | Parris et al. |
| 7,962,101 B2 | 6/2011 | Vaswani et al. |

(56) References Cited

U.S. PATENT DOCUMENTS

| | | | |
|---|---|---|---|
| 7,980,317 B1 | 7/2011 | Preta et al. |
| 8,014,791 B2 | 9/2011 | Guigne et al. |
| 8,047,072 B2 | 11/2011 | Ball |
| 8,082,945 B1 | 12/2011 | White et al. |
| 8,109,131 B2 | 2/2012 | Winter |
| 8,140,667 B2 | 3/2012 | Keyghobad et al. |
| 8,249,042 B2 | 8/2012 | Sparr et al. |
| 8,281,654 B2 | 10/2012 | Ball |
| 8,300,626 B2 | 10/2012 | Thubert et al. |
| 8,351,409 B2 | 1/2013 | Albert et al. |
| 8,391,177 B2 | 3/2013 | Picard |
| 8,407,333 B2 | 3/2013 | Keyghobad |
| 8,549,131 B2 | 10/2013 | Keyghobad et al. |
| 8,660,134 B2 | 2/2014 | Splitz |
| 8,823,509 B2 | 9/2014 | Hyland et al. |
| 8,833,390 B2 | 9/2014 | Ball et al. |
| 8,855,569 B2 | 10/2014 | Splitz |
| 8,931,337 B2 | 1/2015 | Renoud |
| 8,931,505 B2 | 1/2015 | Hyland et al. |
| 9,202,362 B2 | 12/2015 | Hyland |
| 9,604,858 B2 | 3/2017 | Kamen et al. |
| 2001/0010032 A1 | 7/2001 | Ehlers et al. |
| 2001/0013488 A1 | 8/2001 | Fukunaga et al. |
| 2001/0024163 A1 | 9/2001 | Petite |
| 2001/0048030 A1 | 12/2001 | Sharood et al. |
| 2002/0002425 A1 | 1/2002 | Dossey et al. |
| 2002/0013679 A1 | 1/2002 | Petite |
| 2002/0019725 A1 | 2/2002 | Petite |
| 2002/0031101 A1 | 3/2002 | Petite |
| 2002/0051546 A1 | 5/2002 | Bizjak |
| 2002/0062392 A1 | 5/2002 | Nishikawa et al. |
| 2002/0067717 A1 | 6/2002 | Raschke et al. |
| 2002/0073183 A1 | 6/2002 | Yoon et al. |
| 2002/0089802 A1 | 7/2002 | Beckwith |
| 2002/0105346 A1 | 8/2002 | Banks |
| 2002/0130069 A1 | 9/2002 | Moskoff |
| 2002/0130768 A1 | 9/2002 | Che et al. |
| 2002/0149487 A1* | 10/2002 | Haines .............. F17D 5/06 340/605 |
| 2002/0159434 A1 | 10/2002 | Gosior et al. |
| 2002/0169643 A1 | 11/2002 | Petite et al. |
| 2002/0190956 A1 | 12/2002 | Klein et al. |
| 2003/0009515 A1 | 1/2003 | Lee et al. |
| 2003/0018733 A1 | 1/2003 | Yoon et al. |
| 2003/0018776 A1 | 1/2003 | Yoon et al. |
| 2003/0034900 A1 | 2/2003 | Han |
| 2003/0036810 A1 | 2/2003 | Petite |
| 2003/0046377 A1 | 3/2003 | Daum et al. |
| 2003/0074109 A1 | 4/2003 | Jeong et al. |
| 2003/0076241 A1 | 4/2003 | Middleton |
| 2003/0093484 A1 | 5/2003 | Petite |
| 2003/0107485 A1 | 6/2003 | Zoratti |
| 2003/0174070 A1 | 9/2003 | Garrod |
| 2004/0006513 A1* | 1/2004 | Wolfe ............ G01N 33/18 705/22 |
| 2004/0010561 A1 | 1/2004 | Kim et al. |
| 2004/0054747 A1 | 3/2004 | Breh et al. |
| 2004/0064217 A1 | 4/2004 | Addink et al. |
| 2004/0129312 A1 | 7/2004 | Cuzzo et al. |
| 2004/0139210 A1 | 7/2004 | Lee et al. |
| 2004/0154965 A1 | 8/2004 | Baum et al. |
| 2004/0158333 A1 | 8/2004 | Ha et al. |
| 2004/0159149 A1 | 8/2004 | Williams et al. |
| 2004/0183687 A1 | 9/2004 | Petite et al. |
| 2004/0199340 A1 | 10/2004 | Kersey et al. |
| 2005/0009192 A1 | 1/2005 | Page |
| 2005/0067022 A1 | 3/2005 | Istre |
| 2005/0072214 A1 | 4/2005 | Cooper |
| 2005/0078631 A1 | 4/2005 | Cornwell |
| 2005/0084418 A1 | 4/2005 | Hill et al. |
| 2005/0096753 A1 | 5/2005 | Arling |
| 2005/0104747 A1 | 5/2005 | Silic et al. |
| 2005/0121880 A1 | 6/2005 | Santangelo |
| 2005/0159823 A1 | 7/2005 | Hayes |
| 2005/0190784 A1 | 9/2005 | Stine |
| 2005/0195768 A1 | 9/2005 | Petite et al. |
| 2005/0195775 A1 | 9/2005 | Petite et al. |
| 2005/0201379 A1 | 9/2005 | Zhang et al. |
| 2005/0201397 A1 | 9/2005 | Petite |
| 2005/0203647 A1 | 9/2005 | Landry et al. |
| 2005/0246295 A1 | 11/2005 | Cameron |
| 2005/0251367 A1 | 11/2005 | Kahn et al. |
| 2006/0012491 A1 | 1/2006 | Mahowald |
| 2006/0028355 A1 | 2/2006 | Patterson et al. |
| 2006/0041655 A1 | 2/2006 | Holloway et al. |
| 2006/0272830 A1 | 2/2006 | Fima |
| 2006/0046664 A1 | 3/2006 | Paradiso et al. |
| 2006/0059977 A1* | 3/2006 | Kates ................ G01M 3/2815 73/40 |
| 2006/0098576 A1 | 5/2006 | Brownrigg et al. |
| 2006/0122736 A1 | 6/2006 | Alexanian |
| 2006/0158347 A1 | 7/2006 | Roche et al. |
| 2006/0174707 A1 | 8/2006 | Zhang |
| 2006/0181414 A1 | 8/2006 | Bandy et al. |
| 2006/0201550 A1 | 9/2006 | Blyth et al. |
| 2006/0218266 A1 | 9/2006 | Matsumoto et al. |
| 2006/0248961 A1 | 11/2006 | Shachar |
| 2006/0273896 A1 | 12/2006 | Kates |
| 2006/0284784 A1 | 12/2006 | Smith et al. |
| 2007/0035315 A1* | 2/2007 | Hilleary .............. C23F 13/22 324/700 |
| 2007/0059986 A1 | 3/2007 | Rockwell |
| 2007/0063866 A1 | 3/2007 | Webb |
| 2007/0091825 A1 | 4/2007 | Budampati et al. |
| 2007/0219728 A1 | 9/2007 | Papageorgiou et al. |
| 2007/0284293 A1 | 12/2007 | Pitchford et al. |
| 2007/0293221 A1 | 12/2007 | Hwang et al. |
| 2007/0293990 A1 | 12/2007 | Alexanian |
| 2007/0298779 A1 | 12/2007 | Wolman et al. |
| 2008/0030319 A1 | 2/2008 | McKeena et al. |
| 2008/0043637 A1 | 2/2008 | Rahman |
| 2008/0061769 A1 | 3/2008 | Junk et al. |
| 2008/0084260 A1 | 4/2008 | Swartzentruber |
| 2008/0086560 A1 | 4/2008 | Monier |
| 2008/0095403 A1 | 4/2008 | Benhammou |
| 2008/0109090 A1 | 5/2008 | Esmaili et al. |
| 2008/0149180 A1 | 6/2008 | Parris et al. |
| 2008/0150750 A1 | 6/2008 | Parris |
| 2008/0155064 A1 | 6/2008 | Kosuge |
| 2008/0169910 A1 | 7/2008 | Greene et al. |
| 2008/0186898 A1 | 8/2008 | Petite |
| 2008/0189056 A1 | 8/2008 | Heidl et al. |
| 2008/0195329 A1 | 8/2008 | Prince et al. |
| 2008/0240078 A1 | 10/2008 | Thubert |
| 2008/0281534 A1 | 11/2008 | Hurley |
| 2008/0291054 A1 | 11/2008 | Groft |
| 2009/0040057 A1 | 2/2009 | Keyghobad |
| 2009/0044628 A1 | 2/2009 | Lotscher |
| 2009/0058676 A1 | 3/2009 | Orlosky |
| 2009/0066524 A1 | 3/2009 | Yukawa et al. |
| 2009/0068947 A1 | 3/2009 | Petite |
| 2009/0084734 A1 | 4/2009 | Yencho |
| 2009/0121860 A1 | 5/2009 | Kimmel et al. |
| 2009/0123340 A1 | 5/2009 | Knudsen et al. |
| 2009/0133887 A1 | 5/2009 | Garcia et al. |
| 2009/0153357 A1 | 6/2009 | Bushman et al. |
| 2009/0157521 A1 | 6/2009 | Moren |
| 2009/0188313 A1 | 7/2009 | Ball |
| 2009/0215424 A1 | 8/2009 | Petite |
| 2009/0243840 A1 | 10/2009 | Petite et al. |
| 2009/0255346 A1 | 10/2009 | Hendey et al. |
| 2009/0260697 A1 | 10/2009 | Mevius et al. |
| 2009/0271045 A1 | 10/2009 | Savelle et al. |
| 2009/0287838 A1 | 11/2009 | Keyghobad et al. |
| 2009/0287966 A1 | 11/2009 | Keyghobad |
| 2009/0301571 A1 | 12/2009 | Ruhs |
| 2009/0309755 A1 | 12/2009 | Williamson et al. |
| 2009/0319853 A1 | 12/2009 | Keyghobad |
| 2009/0322453 A1 | 12/2009 | Kawaguchi |
| 2010/0017465 A1 | 1/2010 | Brownrigg et al. |
| 2010/0039984 A1 | 2/2010 | Brownrigg |
| 2010/0060479 A1 | 3/2010 | Salter |
| 2010/0156632 A1 | 6/2010 | Hyland et al. |
| 2010/0193430 A1 | 8/2010 | Whiteman |

(56) References Cited

U.S. PATENT DOCUMENTS

| | | |
|---|---|---|
| 2010/0194582 A1 | 8/2010 | Petite |
| 2010/0214120 A1 | 8/2010 | Means |
| 2010/0250054 A1 | 9/2010 | Petite |
| 2010/0265909 A1 | 10/2010 | Petite et al. |
| 2010/0295672 A1 | 11/2010 | Hyland et al. |
| 2010/0312881 A1 | 12/2010 | Davis et al. |
| 2010/0329232 A1 | 12/2010 | Tubb et al. |
| 2011/0018762 A1 | 1/2011 | Walley et al. |
| 2011/0030482 A1 | 2/2011 | Meeusen et al. |
| 2011/0044276 A1 | 2/2011 | Albert et al. |
| 2011/0059462 A1 | 3/2011 | Lim et al. |
| 2011/0079402 A1 | 4/2011 | Darby et al. |
| 2011/0093123 A1 | 4/2011 | Alexanian |
| 2011/0108136 A1 | 5/2011 | Margalit et al. |
| 2011/0125412 A1 | 5/2011 | Salzer et al. |
| 2011/0132484 A1 | 6/2011 | Teach et al. |
| 2011/0140909 A1 | 6/2011 | Olson et al. |
| 2011/0178644 A1 | 7/2011 | Picton |
| 2011/0190947 A1 | 8/2011 | Savelle, Jr. et al. |
| 2011/0215945 A1 | 9/2011 | Peleg et al. |
| 2011/0233935 A1 | 9/2011 | Baarman et al. |
| 2011/0257788 A1 | 10/2011 | Wiemers et al. |
| 2011/0308638 A1 | 12/2011 | Hyland |
| 2012/0007744 A1 | 1/2012 | Pal et al. |
| 2012/0068476 A1 | 3/2012 | Bradfield |
| 2012/0068477 A1 | 3/2012 | Bradfield |
| 2012/0106518 A1 | 5/2012 | Albert et al. |
| 2012/0132445 A1 | 5/2012 | Mallon et al. |
| 2012/0271686 A1 | 10/2012 | Silverman |
| 2012/0298208 A1 | 11/2012 | Taylor et al. |
| 2012/0298381 A1 | 11/2012 | Taylor |
| 2012/0305084 A1 | 12/2012 | Ball |
| 2013/0036800 A1 | 2/2013 | Mohajer |
| 2013/0041601 A1 | 2/2013 | Dintakurti et al. |
| 2013/0083722 A1 | 4/2013 | Bhargava et al. |
| 2013/0094537 A1 | 4/2013 | Hui et al. |
| 2013/0107772 A1 | 5/2013 | Splitz |
| 2013/0109319 A1 | 5/2013 | Splitz et al. |
| 2013/0181848 A1 | 7/2013 | Picard |
| 2013/0214883 A1 | 8/2013 | Yano |
| 2014/0026644 A1 | 1/2014 | Patel et al. |
| 2014/0278246 A1 | 9/2014 | Clark et al. |
| 2014/0340238 A1 | 11/2014 | Hyland |
| 2015/0308627 A1* | 10/2015 | Hoskins ............... E03B 7/00 702/45 |
| 2016/0356755 A1 | 12/2016 | Gifford |
| 2017/0059543 A1 | 3/2017 | Clark |

FOREIGN PATENT DOCUMENTS

| | | |
|---|---|---|
| AU | 2011265675 | 5/2015 |
| AU | 2014259545 | 11/2015 |
| AU | 2015202223 | 9/2016 |
| CA | 2476119 | 2/2005 |
| CA | 2634759 | 12/2009 |
| CN | 1185838 | 6/1998 |
| CN | 204828756 | 12/2015 |
| DE | 19757581 | 7/1998 |
| DE | 202006017758 | 2/2007 |
| EP | 1901253 | 3/2008 |
| GB | 2305333 | 4/1997 |
| JP | 62295674 | 12/1987 |
| JP | 05253316 | 10/1993 |
| JP | 06223279 | 8/1994 |
| JP | 6300606 | 10/1994 |
| JP | 07116285 | 5/1995 |
| JP | 07231363 | 8/1995 |
| JP | 08128079 A * | 5/1996 ............... E03B 1/00 |
| JP | H102744 | 1/1998 |
| JP | 11046254 | 2/1999 |
| JP | H11210028 | 8/1999 |
| JP | 2000131179 | 5/2000 |
| JP | 2000285356 | 10/2000 |
| JP | 2001200952 | 7/2001 |
| JP | 2002310840 | 10/2002 |
| JP | 2002352361 | 12/2002 |
| JP | 2005315663 | 11/2005 |
| JP | 2005321935 | 11/2005 |
| JP | 2006062414 | 3/2006 |
| JP | 2006062716 | 3/2006 |
| JP | 2006285645 | 10/2006 |
| JP | 2007047139 | 2/2007 |
| JP | 2008198044 | 8/2008 |
| JP | 2010068017 | 3/2010 |
| JP | 2012507090 | 3/2012 |
| JP | 2012527706 | 11/2012 |
| JP | 2013528732 | 7/2013 |
| JP | H5654124 | 11/2014 |
| WO | 9810299 | 3/1998 |
| WO | 9810394 | 3/1998 |
| WO | 2008087911 | 7/2008 |
| WO | WO 2009012254 A1 * | 1/2009 ............... G01N 33/18 |
| WO | 2009057214 | 5/2009 |
| WO | 2010051287 | 5/2010 |
| WO | 2010135587 | 11/2010 |
| WO | 2011159403 | 12/2011 |
| WO | 2014151384 | 9/2014 |
| WO | 2016197096 | 12/2016 |

OTHER PUBLICATIONS

Keyghobad, Seyamak; U.S. Patent Application entitled: Method and Apparatus for Inexpensively Monitoring and Controlling Remotely Distributed Appliances for U.S. Appl. No. 13/590,954, filed Aug. 21, 2012, 35 pgs.

Hyland; U.S. Patent Application Entitled: Infrastructure Monitoring Devices, Systems and Methods under U.S. Appl. No. 13/101,235, filed May 5, 2011; 28 pgs.

Hyland, Gregory E., Non-Final Office Action for U.S. Appl. No. 13/101,235, filed May 5, 2011, dated Jul. 31, 2013; 57 pgs.

Hyland, Gregory E.; Final Office Action for U.S. Appl. No. 13/101,235, filed May 5, 2011, dated Feb. 20, 2014; 29 pgs.

Hyland, Gregory E.; Non-Final Office Action for U.S. Appl. No. 13/101,235, filed May 5, 2011, dated Jun. 5, 2014, 29 pgs.

Hyland, Gregory E.; Notice of Allowance for U.S. Appl. No. 13/101,235, filed May 5, 2011, dated Sep. 11, 2014, 11 pgs.

Hyland, Gregory E.; Supplemental Notice of Allowability for U.S. Appl. No. 13/101,235, filed May 5, 2011, dated Nov. 25, 2014, 5 pgs.

Hyland, Gregory E.; Issue Notification for U.S. Appl. No. 13/101,235, filed May 5, 2011, dated Dec. 23, 2014, 1 pg.

Hyland, Gregory E.; U.S. Patent Application entitled: Infrastructure Monitoring Devices, Systems, and Methods having U.S. Appl. No. 14/557,754, filed Dec. 2, 2014, 28 pgs.

Ball, Marty Scott; Mexico Office Action for U.S. Application No. MX/a/2012/006097, filed May 25, 2012, dated Mar. 19, 2015, 3 pgs.

Ball, Marty Scott; Mexico Office Action for U.S. Application No. MX/a/2012/006097, filed May 25, 2012, dated May 26, 2015, 5 pgs.

Hyland; PCT Application entitled: Infrastructure Monitoring System and Method having serial No. PCT/US09/62247, filed Oct. 27, 2009, 30 pgs.

Hyland; International Preliminary Report on Patentability for serial No. PCT/US2009/062247, filed Oct. 27, 2009, dated May 3, 2011, 7 pgs.

International Search Report for serial No. PCT/US2009/062247, filed on Oct. 27, 2009, dated Dec. 18, 2009, 2 pgs.

Hyland, Gregory;Mexico Office Action for serial No. MX/a/2011/004330, filed Apr. 25, 2011, dated Mar. 21, 2013, 7 pgs.

Hyland, Gregory; Mexico Office Action for serial No. MX/a/2011/004330, filed Apr. 25, 2011, dated Jul. 18, 2013, 6 pgs.

Hyland, Gregory; Mexico Office Action for serial No. MX/a/2011/004330, filed Apr. 25, 2011, dated Oct. 3, 2013, 6 pgs.

Hyland; European Search Report for serial No. EP09824079.9, filed Oct. 27, 2009, dated May 8, 2012; 38 pages.

Hyland, Gregory E.; Issue Notification for U.S. Appl. No. 12/606,957, filed Oct. 27, 2009, dated Nov. 11, 2015, 1 pg.

Ball, Marty Scott; Issue Notification for U.S. Appl. No. 13/149,720, filed May 31, 2011, dated Aug. 27, 2014, 1 pg.

(56) References Cited

OTHER PUBLICATIONS

Ball, Marty Scott; Non-Final Office Action for U.S. Appl. No. 13/149,720, filed May 31, 2011, dated Mar. 11, 2014, 75 pgs.
Ball, Marty Scott; Notice of Allowance for U.S. Appl. No. 13/149,720, filed May 31, 2011, dated Jun. 24, 2014, 29 pgs.
Ball, Marty Scott; Supplemental Notice of Allowability for U.S. Appl. No. 13/149,720, filed May 31, 2011, dated Aug. 12, 2014, 4 pgs.
Ball, Marty Scott; U.S. Patent Application Entitled: Valve Meter Assembly and Method under U.S. Appl. No. 13/149,720, filed May 31, 2011; 56 pgs.
Ball, Marty Scott; U.S. Patent Application Entitled: Valve Meter Assembly and Method, U.S. Appl. No. 14/451,896, filed Aug. 5, 2014; 56 pgs.
Hyland, Gregory E.; Applicant Initiated Interview Summary for U.S. Appl. No. 12/606,957, filed Oct. 27, 2009, dated Feb. 18, 2014, 4 pgs.
Hyland, Gregory E.; Final Office Action for U.S. Appl. No. 12/606,957, filed Oct. 27, 2009, dated Dec. 17, 2013, 54 pgs.
Hyland, Gregory E.; Final Office Action for U.S. Appl. No. 12/606,957, filed Oct. 27, 2009, dated Apr. 10, 2013, 80 pgs.
Hyland, Gregory E.; Final Office Action for U.S. Appl. No. 12/606,957, filed Oct. 27, 2009, dated Sep. 22, 2014, 49 pgs.
Hyland, Gregory E.; Non-Final Office Action for U.S. Appl. No. 12/606,957, filed Oct. 27, 2009, dated Oct. 18, 2012; 44 pgs.
Hyland, Gregory E.; Non-Final Office Action for U.S. Appl. No. 12/606,957, filed Oct. 27, 2009, dated Apr. 8, 2014, 43 pgs.
Hyland, Gregory E.; Non-Final Office Action for U.S. Appl. No. 12/606,957, filed Oct. 27, 2009, dated Sep. 6, 2013; 53 pgs.
Hyland, Gregory E.; Non-Final Office Action for U.S. Appl. No. 12/606,957, filed Oct. 27, 2009, dated Apr. 16, 2015, 47 pgs.
Hyland, Gregory E.; Notice of Allowance for U.S. Appl. No. 12/606,957, filed Oct. 27, 2009, dated Jul. 27, 2015, 19 pgs.
Hyland, Gregory E.; Supplemental Notice of Allowability for U.S. Appl. No. 12/606,957, filed Oct. 27, 2009, dated Oct. 13, 2015, 4 pgs.
Hyland; U.S. Patent Application entitled: Infrastructure Monitoring System and Method, having U.S. Appl. No. 12/606,957, filed Oct. 27, 2009, 30 pgs.
Hyland, Gregory; U.S. Continuation Application entitled: Infrastructure Monitoring Devices, Systems, and Methods having U.S. Appl. No. 14/848,676, filed Sep. 9, 2015, 29 pgs.
Hyland, Gregory E.; Final Office Action for U.S. Appl. No. 12/784,300, filed May 20, 2010, dated Feb. 11, 2014; 37 pgs.
Hyland, Gregory E.; Final Office Action for U.S. Appl. No. 12/784,300, filed May 20, 2010, dated May 29, 2013, 71 pgs.
Hyland, Gregory E.; Issue Notification for U.S. Appl. No. 12/784,300, filed May 20, 2010, dated Aug. 13, 2014. 1 pg.
Hyland, Gregory E.; Non-Final Office Action for U.S. Appl. No. 12/784,300, filed May 20, 2010, dated Sep. 10, 2012, 35 pgs.
Hyland, Gregory E.; Notice of Allowance for U.S. Appl. No. 12/784,300, filed May 20, 2010, dated Apr. 23, 2014, 20 pgs.
Hyland, Gregory E.; Supplemental Notice of Allowability for U.S. Appl. No. 12/784,300, filed May 20, 2010, dated Aug. 1, 2014, 4 pgs.
Hyland; U.S. Application entitled: Infrastructure Monitoring Devices, Systems, and Methods, having U.S. Appl. No. 12/784,300, filed May 20, 2010, 32 pgs.
Hyland, Gregory E.; U.S. Continuation Application entitled: Infrastructure Monitoring Devices, Systems, and Methods, having U.S. Appl. No. 14/450,452, filed Aug. 4, 2014, 32 pgs.
Keyghobad, Seyamak; Issue Notification for U.S. Appl. No. 10/298,300, filed Nov. 18, 2002, dated Oct. 8, 2008; 1 pg.
Keyghobad, Seyamak; Requirement for Restriction/ Election for U.S. Appl. No. 10/298,300, filed Nov. 18, 2002; dated Feb. 9, 2006; 11 pages.
Keyghobad, Seyamak; Issue Notification for U.S. Appl. No. 12/243,452, filed Oct. 1, 2008 dated Jun. 16, 2010; 1 pg.
Keyghobad, Seyamak; Issue Notification for U.S. Appl. No. 12/490,867, filed Jun. 24, 2009, dated Feb. 29, 2012; 1 pg.

Keyghobad, Seyamak; Non Final Rejection for U.S. Appl. No. 12/490,867, filed Jun. 24, 2009, dated Mar. 21, 2011; 9 pgs.
Keyghobad, Seyamak; Non Final Rejection for U.S. Appl. No. 12/490,867, filed Jun. 24, 2009, dated Oct. 4, 2010; 13 pgs.
Hyland, Gregory E.; Non-Final Office Action for U.S. Appl. No. 12/784,300, filed May 20, 2010, dated Sep. 24, 2013; 37 pgs.
Keyghobad, Seyamak; Notice of Allowance for U.S. Appl. No. 12/490,867, filed Jun. 24, 2006, dated Sep. 7, 2011; 6 pgs.
Keyghobad, Seyamak; Notice of Allowance for U.S. Appl. No. 12/490,867, filed Jun. 24, 2009, dated Nov. 2, 2011; 17 pgs.
Keyghobad, Seyamak; U.S. Patent Application Entitled: Method and Apparatus for Inexpensively Monitoring and Controlling Remotely Distributed Appliances under U.S. Appl. No. 12/490,867, filed Jun. 24, 2009; 33 pgs.
U.S. Application Keyghobad, Seyamak; Issue Notification for U.S. Appl. No. 12/490,925, filed Jun. 24, 2009; dated Aug. 18, 2010; 1 pg.
Keyghobad, Seyamak; Non-final office action for U.S. Appl. No. 12/490,925, filed Jun. 24, 2009; dated Dec. 23, 2009; 17 pgs.
Keyghobad, Seyamak; Notice of Allowance for U.S. Appl. No. 12/490,925, filed Jun. 24, 2009, dated Aug. 2, 2010, 8 pgs.
Keyghobad, Seyamak; Issue Notification for U.S. Appl. No. 12/490,957, filed Jun. 24, 2009; dated Aug. 4, 2010; 1 pg.
Keyghobad, Seyamak; U.S. Patent Application Entitled: Method and Apparatus for Inexpensively Monitoring and Controlling Remotely Distributed Appliances under U.S. Appl. No. 12/490,957, filed Jun. 24, 2009; 33 pgs.
Keyghobad, Seyamak; Non-final Office Action for U.S. Appl. No. 13/372,408, filed Feb. 23, 2012; dated May 25, 2012; 17 pgs.
Keyghobad, Seyamak; Notice of Allowance for U.S. Appl. No. 13/372,408, filed Feb. 13, 2012, dated Jul. 27, 2012; 11 pgs.
Keyghobad, Seyamak; Issue Notification for U.S. Appl. No. 13/372,408, filed Feb. 13, 2012, dated Mar. 6, 2013, 1 pg.
Keyghobad, Seyamak; Notice of Allowance for U.S. Appl. No. 13/372,408, filed Feb. 13, 2012; dated Nov. 1, 2012; 18 pgs.
Keyghobad, Seyamak; Supplemental Notice of Allowance for U.S. Appl. No. 13/372,408, filed Feb. 13, 2012; dated Aug. 2, 2012; 7 pgs.
Keyghobad, Seyamak; U.S. Patent Application Entitled: Method and Apparatus for Inexpensively Monitoring and Controlling Remotely Distributed Appliances under U.S. Appl. No. 13/372,408, filed Feb. 13, 2012; 34 pgs.
Keyghobad, Seyamak, Issue Notification for U.S. Appl. No. 13/590,954, filed Aug. 21, 2012, dated Sep. 11, 2013, 1 pg.
Keyghobad, Seyamak; Non-Final Office Action for U.S. Appl. No. 13/590,954, filed Aug. 21, 2012, dated Dec. 13, 2012; 39 pgs.
Keyghobad, Seyamak; Notice of Allowance for U.S. Appl. No. 13/590,954, filed Aug. 21, 2012, dated Mar. 21, 2013, 22 pgs.
Splitz, David Edwin; Notice of Allowance for U.S. Appl. No. 13/283,526, filed Oct. 27, 2011, dated Oct. 9, 2013, 16 pgs.
Splitz, David Edwin; Issue Notification for U.S. Appl. No. 13/283,526, filed Oct. 27, 2011, dated Feb. 5, 2014, 1 pg.
Splitz, David E.; U.S. Patent Application Entitled: Systems and Methods for Dynamic Squelching in Radio Frequency Devices assigned U.S. Appl. No. 13/339,655, filed Dec. 29, 2011; 50 pgs.
Splitz, David Edwin; Non-Final Office Action for U.S. Appl. No. 13/339,655, filed Dec. 29, 2011, dated Sep. 16, 2013, 57 pgs.
Splitz, David Edwin; Non-Final Office Action for U.S. Appl. No. 13/339,655, filed Dec. 29, 2011, dated Mar. 5, 2014, 18 pgs.
Splitz, David Edwin; Notice of Allowance for U.S. Appl. No. 13/339,655, filed Dec. 29, 2011, dated May 23, 2014, 41 pgs.
Splitz, David Edwin; Issue Notification for U.S. Appl. No. 13/339,655, filed Dec. 29, 2011, dated Sep. 17, 2014, 1 pg.
Splitz, David Edwin; U.S. Patent Application entitled: Systems and Methods for Recovering an Out-of-Service Node in a Hierarchical Network, U.S. Appl. No. 14/490,081, filed Sep. 18, 2014, 51 pgs.
Dukes, Brent; U.S. Application entitled: Dynamic Routing in a Mesh Network, having U.S. Appl. No. 14/475,050, filed Sep. 2, 2014, 42 pgs.
Splitz, David; International Search Report and Written Opinion for serial No. PCT/US11/58260, filed Oct. 28, 2011, dated Feb. 7, 2012, 8 pgs.

(56) References Cited

OTHER PUBLICATIONS

Splitz, David; PCT Application entitled: Systems and Methods for Time-Based Hailing of Radio Frequency having serial No. PCT/US11/058260, filed Oct. 28, 2011, 51 pgs.
Splitz, David; International Preliminary Report on Patentability for serial No. PCT/US11/58260, filed Oct. 28, 2011, dated May 8, 2014, 7 pgs.
Splitz, David; International Search Report and Written Opinion for serial No. PCT/US12/22060, filed Jan. 20, 2012, dated Mar. 29, 2012, 8 pgs.
Splitz, David; PCT Application entitled: Systems and Methods for Dynamic Squelching in Radio Frequency Devices having serial No. PCT/US12/022060, filed Jan. 20, 2012, 50 pgs.
Splitz, David; International Preliminary Report on Patentability for serial No. PCT/US12/22060, filed Jan. 20, 2012, dated May 8, 2014, 6 pgs.
Splitz, David Edwin; Extended European Search Report for serial No. 12844451.0, filed Jan. 20, 2012, dated Apr. 21, 2015, 8 pgs.
Dukes, Brent; PCT Application entitled: Dunamic Ruoting in a Mesh Network having serial No. PCT/US15/44140, filed Aug. 7, 2015, 41 pgs.
Splitz, David Edwin; U.S. Provisional Patent Application entitled: Automatic Discovery of Nodes in a Mesh Network, U.S. Appl. No. 61/779,892, filed Mar. 13, 2013; 110 pgs.
Vonroll Hydro—Hydrojournal, pp. 1-16, May 2008.
English Translation: Vonroll Hydro—Hyrdojournal, Technology with a Future for Shut-off Systems—p. 4, VonRoll Hydro (shop) GmbH—New Concepts for Apprentice Training—p. 12, May 2008.
Von Roll Hydro—Hydrojournal, pp. 1-16, Nov. 2008.
English Translation: Von Roll Hydro—Hyrdojournal,VonRoll Hydroalert—Provides a Warning in the Event of Any Tampering with the Water Supply, p. 3, Nov. 2008.
Keyghobad, Seyamak; Examiner Interview Summary Record for U.S. Appl. No. 10/298,300, filed Nov. 18, 2002; dated Feb. 5, 2008; 2 pages.
Keyghobad, Seyamak; Non-Final Rejection for U.S. Appl. No. 10/298,300, filed Nov. 18, 2002; dated Oct. 26, 2007; 35 pages.
Keyghobad, Seyamak; Requirement for Restriction/ Election for U.S. Appl. No. 10/298,300, filed Nov. 18, 2002; dated Feb. 27, 2006; 17 pages.
Keyghobad,Seyamak; U.S. Patent Application entitled: Method and Apparatus for Inexpensively Monitoring and Controlling Remotely Distributed Appliances under U.S. Appl. No. 10/298,300, filed Nov. 18, 2002; 40 pages.
Keyghobad, Seyamak; Non-Final Rejection for U.S. Appl. No. 10/298,300, filed Nov. 18, 2002; dated May 18, 2006; 13 pages.
Keyghobad, Seyamak; Non-Final Rejection for U.S. Appl. No. 10/298,300, filed Nov. 18, 2002; dated Jun. 6, 2007; 32 pages.
Keyghobad, Seyamak; Certificate of Correction for U.S. Appl. No. 10/298,300, filed Nov. 18, 2002; dated Mar. 31, 2009; 1 page.
Keyghobad, Seyamak; Notice of Allowance for U.S. Appl. No. 10/298,300, filed Nov. 18, 2002; dated Jul. 14, 2008; 4 pages.
Keyghobad, Seyamak; Notice of Allowance for U.S. Appl. No. 12/243,452, filed Oct. 1, 2008; dated Mar. 22, 2010; 8 pages.
Keyghobad, Seyamak; Examiner Interview Summary Record for U.S. Appl. No. 12/243,452, filed Oct. 1, 2008; dated Dec. 7, 2009; 3 pages.
Keyghobad, Seyamak; Non-Final Rejection for U.S. Appl. No. 12/243,452, filed Oct. 1, 2008; dated Sep. 14, 2009; 12 pages.
Keyghobad,Seyamak; Non-Final Rejection for U.S. Appl. No. 12/243,452, filed Oct. 1, 2008; dated May 1, 2009; 5 pages.
Keyghobad, Seyamak; U.S. Patent Application Entitled: Method and Apparatus for Inexpensively Monitoring and Controlling Remotely Distributed Appliancesl under U.S. Appl. No. 12/243,452, filed Oct. 1, 2008; 33 pages.
Keyghobad, Seyamak; Notice of Allowance for U.S. Appl. No. 12/490,925, filed Jun. 24, 2009; dated Jul. 19, 2010; 8 pages.
Keyghobad, Seyamak; U.S. Patent Application Entitled: Method and Apparatus for Inexpensively Monitoring and Controlling Remotely Distributed Appliances under U.S. Appl. No. 12/490,925, filed Jun. 24, 2009; 33 pgs.
Keyghobad, Seyamak; Notice of Allowance for U.S. Appl. No. 12/490,957, filed Jun. 24, 2009; dated Jun. 24, 2010; 10 pgs.
Keyghobad,Seyamak; Non-Final Rejection for U.S. Appl. No. 12/490,957, filed Jun. 24, 2009; dated Dec. 23, 2009; 17 pgs.
Young et al. "Real-Time Intranet-Controlled Virtual Instrument Multiple-Circuit Power Monitoring," IEEE Transactions on Instrumentation and Measurement, Jun. 2000. vol. 49, No. 3, p. 570. [Accessed Dec. 29, 2011] http://ieeexplore.ieee.org/xpls/abs_all.jsp?.
De Almeida et al. "Advanced Monitoring Technologies for the Evaluation of Demand-Side Management Programs," IEEE Transactions on Power Systems, Aug. 1994. vol. 9, No. 3. [Accessed Dec. 29, 2011] http://ieeexplore.ieee.org/xpls/abs_all.jsp?arnumber=336086.
Dolezilek. "Microprocessor Based Relay Information Improves the Power System," Rural Electric Power Conference, May 1999. p. B5/1-B5/9. [Accessed Dec. 29, 2011] http://ieeexplore.ieee.org/xpls/abs_all.jsp?arnumber=768685.
Gehami et al. "Electronic Control System I Salient Feature in Substation," Transmission & Distrubition, Mar. 1991. vol. 43, No. 3, p. 48. [Accessed Dec. 29, 2011—ProQuest].
Horlent. "New Metering and Reading Techniques Based on a Modular Design Concept," 10th International Conference on Electricity Distribution, May 1989. vol. 5, p. 455-459. [Accessed Dec. 29, 2011—IEEExplore].
"In Brief," Land Mobile Radio News, Jan. 16, 1998. vol. 52, No. 3, p. 1. [Accessed Dec. 29, 2011—ProQuest] http://proquest.umi.com/pqdweb?did=25435781&sid=1&Fmt=3&clientId=31810&RQT=309&VName%20=PQD.
"Landis & Gyr Utilities: Service Partnership Helps Utilities Use Available Resources More Effectively," www.landisgyr.com/utilities/e/fr_press1_e.htm (archived Feb. 6, 1998) http://web.archive.org/web/19980206060801/http://www.landisgyr.com/utilities.
Tamarkin. "Automated Meter Reading", Sep.-Oct. 1992, vol. 50, No. 5/ [Accessed Dec. 29, 2011] http://www.usclcorp.com/news/Automatic_Power_reading.pdf.
ANSI; "Protocol Specification for ANSI Type 2 Optical Port", American National Standard, ANSI C.12.18-2006, 11 pgs.
Federal Communications Commission; "Understanding the FCC Regulations for Low-Power, Non-Licensed Transmitters", Office of Engineering and Technology; Oct. 1993; 34 pgs.
Keyghobad, Seyamak; Notice of Allowance for U.S. Appl. No. 12/490,925, filed Jun. 24, 2009; dated Jun. 28, 2010; 10 pgs.
Patterson, Tim; Request for Ex Parte Reexamination under U.S. Appl. No. 90/012,468, filed Sep. 6, 2012; 52 pgs.
Patterson, Tim; Request for Ex Parte Reexamination under U.S. Appl. No. 90/012,449, filed Aug. 23, 2012; 51 pgs.
Radix Corporation; "Automatic Meter Reading", 2 pgs.
Transparent Technologies; "Model M1A: Utility Radio Transmitter; M1A Operating Instructions"; 7 pgs.
Trace; "Pit Water-Meter Transponder"; User Guide; Jan. 2003 16 pgs.
Antenna. Merriam-Webster Dictionary, 2014 [retrieved on Jun. 1, 2014]. Retrieved from the Internet: <URL: www.merriam-webster.com/dictionary/antenna>.
Hyland, Gregory E.;Japanese Office Action for serial No. 2011-533427, filed Oct. 27, 2009, dated Apr. 30, 2013, 15 pgs.
Hyland, Gregory E.; Japanese Office Action for serial No. 2011-533427, filed Oct. 27, 2009, dated Feb. 4, 2014, 50 pgs.
Hyland, Gregory E.; Australian Examination Report for serial No. 2014259545, filed Oct. 27, 2009, dated Jun. 10, 2015; 2 pgs.
Hyland; PCT Application entitled: Infrastructure Monitoring Devices, Systems, and Methods having serial No. PCT/US2010/035666, filed May 20, 2010; 31 pgs.
Hyland, Gregory E.; Decision of Rejection for Japanese serial No. 2011-533427, filed Oct. 27, 2009, dated Sep. 16, 2014, 4 pgs.
Hyland; International Preliminary Report on Patentability for serial No. PCT/US2010/035666, filed May 20, 2010, dated Nov. 22, 2011, 6 pgs.

(56) References Cited

OTHER PUBLICATIONS

Hyland, Gregory E.; Mexico Office Action for serial No. MX/A/2011/012383, filed May 20, 2010, dated Oct. 8, 2012, 3 pgs.
Hyland, Gregory E.; Mexico Office Action for serial No. MX/A/2011/012383, filed May 20, 2010, dated May 9, 2013, 8 pgs.
Hyland, Gregory E.; Mexico Office Action for serial No. MX/A/2011/012383, filed May 20, 2010, dated Sep. 3, 2013, 10 pgs.
Hyland, Gregory E.; Mexico Final Office Action for serial No. MX/A/2011/012383, filed May 20, 2010, dated Jan. 9, 2014, 9 pgs.
Hyland; International Search Report and Written Opinion for serial No. PCT/US2010/035666, filed May 20, 2010, dated Jul. 16, 2010, 7 pgs.
European Search Report for serial No. EP2433440, filed Nov. 18, 2011, dated Nov. 21, 2012, 6 pgs.
Hyland, Gregory E.; Australian Patent Examination report for serial No. 2010249499, filed Nov. 17, 2011, dated Jun. 16, 2014, 5 pgs.
Hyland, Gregory E.; Australian Patent Examination report for serial No. 2010249499, filed Nov. 17, 2011, dated Nov. 21, 2014, 5 pgs.
Hyland, Gregory; Japanese Office Action for serial No. 2012-512048, filed May 20, 2010, dated Oct. 22, 2013, 51 pgs.
Hyland, Gregory; Decision of Rejection for Japanese serial No. 2012-512048, filed May 20, 2010, dated Apr. 22, 2014, 10 pgs.
Hyland, Gregory; Mexico Office Action for serial No. MX/a/2012/015236, filed Dec. 19, 2012, dated Jun. 13, 2013, 4 pgs.
Hyland, Gregory; Mexico Office Action for serial No. MX/a/2012/015236, filed Dec. 19, 2012, dated Oct. 3, 2013, 8 pgs.
Hyland, Gregory; Mexico Office Action for serial No. MX/a/2012/015236, filed Dec. 19, 2012, dated Dec. 3, 2013, received by foreign associate on Jan. 9, 2014, 4 pgs.
Hyland; International Search Report and Written Opinion for serial No. PCT/US2011/035374, filed May 5, 2011, dated Sep. 13, 2011; 7 pgs.
Hyland; PCT Application Entitled: Infrastructure Monitoring Devices, Systems, and Methods having serial No. PCT/US11/35374, filed May 5, 2011, 28 pgs.
Hyland; International Preliminary Report on Patentability for serial No. PCT/US2011/035374, filed May 5, 2011, dated Dec. 19, 2012; 5 pgs.
Hyland, Gregory E.; Australian Patent Examination Report for serial No. 2011265675, filed Jan. 21, 2012, dated Oct. 1, 2014, 3 pgs.
Hyland, Gregory E.; Japanese Office Action for serial No. 2013515338, filed Jan. 30, 2012, dated Jun. 10, 2014, 8 pgs.
Hyland, Gregory E.; Japanese Office Action for serial No. 2014-234642, filed May 5, 2011, dated Jul. 7, 2015, 9 pgs.
Hyland; U.S. Provisional Patent Application entitled: Water Supply Infrastructure Monitoring System and Method, having U.S. Appl. No. 61/108,770, filed Oct. 27, 2008, 11 pgs.
Hyland; U.S. Provisional Patent Application entitled: Water Supply Infrastructure Monitoring System and Method, having U.S. Appl. No. 61/180,600, filed May 22, 2009, 14 pgs.
Hyland; U.S. Provisional Patent Application entitled: Infrastructure Monitoring Devices, Systems, and Methods, having U.S. Appl. No. 61/355,468, filed Jun. 16, 2010; 31 pgs.
Splitz, David. E.; U.S. Patent Application Entitled: Systems and Methods for Time-Based Hailing of Radio Frequency Devices assigned U.S. Appl. No. 13/283,526, filed Oct. 27, 2011, 51 pages.
Splitz, David Edwin; Non-Final Office Action for U.S. Appl. No. 13/283,526, filed Oct. 27, 2011, dated Jun. 18, 2013, 67 pgs.
Hyland, Gregory; Australian Patent Examination Report for serial No. 2009308949, filed Oct. 27, 2009, dated Nov. 12, 2013, 3 pgs.
Hyland, Gregory; Japanese Office Action for serial No. 2014-234642, filed May 5, 2011, dated Nov. 4, 2015, 9 pgs.
Ball, Marty Scott, Notice of Allowance for U.S. Appl. No. 12/326,240, filed Jan. 20, 2009, dated Aug. 9, 2010, 10 pgs.
Ball, Marty Scott; Issue Notification for U.S. Appl. No. 12/356,240, filed Jan. 20, 2009, dated Dec. 1, 2010; 1 pg.
Ball, Marty Scott; U.S. Patent Application Entitled: Plastic Water Metwr With Metal Threads under U.S. Appl. No. 12/356,240, filed Jan. 20, 2009; 17 pgs.
Ball, Marty Scott; Issue Notification for U.S. Appl. No. 12/947,272, filed Nov. 16, 2010, dated Oct. 12, 2011; 1 pg.
Ball, Marty Scott; Non-Final Office Action for U.S. Appl. No. 12/947,272, filed Nov. 16, 2010, dated May 2, 2011; 11 pgs.
Ball, Marty Scott; Notice of Allowance for U.S. Appl. No. 12/947,272, filed Nov. 16, 2010, dated Aug. 10, 2011; 5 pgs.
Ball, Marty Scott; U.S. Patent Application Entitled: Plastic Water Meter With Metal Threads under U.S. Appl. No. 12/947,272, filed Nov. 16, 2010; 15 pgs.
Ball, Marty Scott, Notice of Allowance for U.S. Appl. No. 13/220,739, filed Aug. 30, 2011, dated May 7, 2012; 10 pgs.
Ball, Marty Scott; Issue Notification for U.S. Appl. No. 13/220,739, filed Aug. 30, 2011, dated Sep. 19, 2012; 1 pg.
Ball, Marty Scott; Miscellaneous Communication to Applicant for U.S. Appl. No. 13/220,739, filed Aug. 30, 2011; dated Jun. 14, 2012; 4 pgs.
Ball, Marty Scott; Notice of Allowance for U.S. Appl. No. 13/220,739, filed Aug. 30, 2011, dated Feb. 17, 2012; 5 pgs.
Ball, Marty Scott; Notice of Allowance for U.S. Appl. No. 13/220,739, filed Aug. 30, 2011, dated Aug. 23, 2012; 9 pgs.
Ball, Marty Scott; U.S. Patent Application Entitled: Plastic Water Meter With Metal Threads; under U.S. Appl. No. 13/220,739, filed Aug. 30, 2011; 14 pgs.
Ball; Non-Final Office Action for U.S. Appl. No. 13/220,739, filed Aug. 30, 2011, dated Nov. 15, 2011, 7 pgs.
Ball, Marty Scott; Non-Final Office Action for U.S. Appl. No. 13/646,892, filed Oct. 8, 2012, dated Jun. 7, 2013; 10 pgs.
Ball, Marty Scott; Notice of Allowance for U.S. Appl. No. 13/646,892, filed Oct. 8, 2012, dated Sep. 17, 2013, 6 pgs.
Ball, Marty Scott; U.S. Continuation Application entitled: Non-Metallic Enclusure With Metal Threads, U.S. Appl. No. 13/646,892, filed Oct. 8, 2012, 14 pgs.
Ball, Marty Scott, Office Action from Canadian Intellectual Property Office for Application No. 2,650,174, filed Jan. 19, 2009, dated Sep. 8, 2011, 3 pgs.
Ball, Marty Scott, Office Action from Canadian Intellectual Property Office for serial No. 2,650,174, filed Jan. 19, 2009, dated Dec. 7, 2010; 2 pages.
Ball, Marty Scott; Canadian Office Action for serial No. 2,777,585, filed Jan. 19, 2009, dated Oct. 21, 2013, 2 pgs.
Hyland, Gregory E.; Canadian Office Action for serial No. 2,741,843, filed Oct. 27, 2009, dated Dec. 8, 2015, 5 pgs.
Ball, Marty Scott; U.S. Provisional Patent Application Entitled: Plastic Water Meter, under U.S. Appl. No. 61/022,088, filed Jan. 18, 2008, 10 pgs.
McCraven, Jeremy; Non-Final Office Action for U.S. Appl. No. 14/273,823, filed May 9, 2014, dated Dec. 8, 2015, 18 pgs.
McCraven, Jeremy; U.S. Patent Application Entitled: Mechanical Stop for Actuator and Orifice, U.S. Appl. No. 14/273,823, filed May 9, 2014, 40 pgs.
Dukes, Brent; International Search Report and Written Opinion for application No. PCT/US15/44140, filed Aug. 7, 2015, dated Dec. 30, 2015, 15 pgs.
Article entitled, "GF Piping Systems' New Metal-to-Plastic Transition Fittings Provide Strong, Leak-Proof Seals", Nov. 13, 2007, pp. 1-6; http://news.thomasnet.com/fullstory/536342.
Brochure entitled, "DoubleSafe tm Transition Fittings from GF Piping Systems" Georg Fischer Piping Systems; date unknown when published: accessed on Oct. 1, 2008; pp. 1-2 http://www.us.piping.georgefischer.com/go/F017C7DA19993E1D340739AFBC4B677E?action=GF_Docu.
Brochure entitled, "POLYRAC and POLYFAST", date unknown when published; accessed on Jun. 1, 2009; pp. 1-8; http://www.cn.piping.georgfischer.com/doc/doc_download.cfm?B81010EAD60EB5F06E54F6B04231161F.
Brochure entitled, "Section 1, Schedule 80 PVC Piping System," Mar. 27, 2006, pp. 1.1-1.32; http://web.archive.org/web/20060816045129/http://www.gfpiping.com/downloads/vinyls/01-Sch80PVC.pdf.
Brochure entitled, "Section 2, Schedule 80 CPVC Piping System," Mar. 27, 2006, pp. 2.1-2.28; http://web.archive.org/web/20060816045129/http://www.gfpiping.com/downloads/vinyls/02-Sch80CPVC.pdf.

(56) References Cited

OTHER PUBLICATIONS

Brochure entitled, "The World Needs Solutions, We Have Them!," date unknown when published' accessed on Oct. 1, 2008; pp. 1-12; http://www.plasticsystems.co.nz/booklets/Civil%20Infrastructure/+GF+%20Utilities%20Brochure.pdf.
Brochure entitled, "Transition Fittings, Strong and Reliable Metal-to-Plastic Transitions", BR-2-0305; date unknown when published; accessed on Oct. 1, 2008; pp. 1-2 http://plascowelding.com/pdf2007/PVC&CPVCPipeandFittings/Thermoplastic-Fittings/PVC&CPVC-Metal.
Hyland, Gregory E.; Non-Final Office Action for U.S. Appl. No. 14/557,754, filed Dec. 2, 2014, dated Jan. 19, 2016, 101 pgs.
Hyland; European Examination Report for serial No. EP09824079.9, filed Oct. 27, 2009, dated Nov. 13, 2015; 6 pgs.
McCraven, Jeremy; Applicant Interview Summary for U.S. Appl. No. 14/273,823, filed May 9, 2014, dated Jan. 12, 2016, 3 pgs.
Ball, Marty Scott; Non-Final Office Action for U.S. Appl. No. 14/451,896, filed Aug. 5, 2014, dated Mar. 18, 2016, 98 pgs.
Hyland, Gregory E.; Non-Final Office Action for U.S. Appl. No. 14/450,452, filed Aug. 4, 2014, dated Feb. 17, 2016, 98 pgs.
Hyland, Gregory; Non-Final Office Action for U.S. Appl. No. 14/848,676, filed Sep. 9, 2015, dated Mar. 4, 2016, 94 pgs.
McCraven, Jeremy; Non-Final Office Action for U.S. Appl. No. 14/273,823, filed May 9, 2014, dated Apr. 12, 2016, 86 pgs.
Ball, Marty Scott; Non-Final Office Action for U.S. Appl. No. 14/451,896, filed Aug. 5, 2014, dated May 12, 2016; 15 pages.
Hyland, Gregory E.; Final Office Action for U.S. Appl. No. 14/557,754, filed Dec. 2, 2014, dated Jun. 30, 2016, 24 pgs.
Hyland, Gregory E.; Mexico Office Action for serial No. MX/a/2012/000347, filed May 5, 2011, dated May 30, 2016, 4 pgs.
Dukes, Brent; Non-Final Office Action for U.S. Appl. No. 14/475,050, filed Sep. 2, 2014, dated May 19, 2016, 119 pgs.
McCraven, Jeremy; Notice of Allowance for U.S. Appl. No. 14/273,823, filed May 9, 2014, dated Jul. 7, 2016, 10 pgs.
Hyland, Gregory E.; Final Office Action for U.S. Appl. No. 14/450,452, filed Aug. 4, 2014, dated Aug. 23, 2016, 41 pgs.
Hyland, Gregory E.; Canadian Office Action for serial No. 2,741,843, filed Oct. 27, 2009, dated Jul. 22, 2016, 5 pgs.
Clark, Kenneth A.; U.S. Patent Application entitled: Systems for Measuring Priorities of Water in a Water Distribution System, U.S. Appl. No. 14/209,257, filed Mar. 13, 2014; 60 pgs.
Clark, Kenneth A.; International Preliminary Report on Patentability for PCT/US2014/025617, filed Mar. 13, 2014, dated Sep. 24, 2015, 12 pgs.
Clark, Kenneth A.; International Search Report and Written Opinion for serial No. PCT/US2014/025617, filed Mar. 13, 2014, dated Aug. 27, 2014, 48 pgs.
Clark, Kenneth A.; PCT Application entitled: Systems for Measuring Properties of Water in a Water Distribution System, having serial No. PCT/US2014/025617, filed Mar. 13, 2014, 58 pgs.
Huang, et al.; "The Mahalanobis-Taguchi system—Neural network algorithm for data mining in dynamic environments", Extern Systems with Appklications (online), 2009 [retrieved on Aug. 13, 2014], vol. 36, pp. 5475-5480.
Clark, Kenneth A.; U.S. Provisional Patent Application entitled: Systems for Measuring Properties of Water in a Water Distribution System , U.S. Appl. No. 61/794,616, filed Mar. 15, 2013; 49 pgs.
Clark, Kenneth A.; Extended European Search Report for serial No. 14771115.4, filed Mar. 13, 2014, dated Sep. 14, 2016, 8 pgs.

Palau, et al.; Article entitled: "Using Multivariate Principal Component Analysis of Injected Water Flows to Detect Anomalous Behaviors in a Water Supply System. A Case Study.", Water Science and Technology: Water Supply, vol. 4, No. 3, Jun. 30, 2004, 12 pgs.
Perelman, et al.; Article entitled: "Event Detection in Water Distribution Systems from Multivariate Water Quality Time Series", Environmental Science & Technology, vol. 46, No. 15, Aug. 7, 2012, 8 pgs.
Stoianov, et al.; Article entitled: "Sensor Networks for Monitoring Water Supply and Sewer Systems: Lessons from Boston", Water Distribution Systems Analysis Symposium 2006; , Aug. 27-30, 2006, 17 pgs.
Gifford, Paul; PCT Application entitled: Distribution System Monitoring, having serial No. PCT/US16/36007, filed Jun. 6, 2016, 53 pgs.
Hyland, Gregory E.; Office Action for Canadian application No. 2,772,545, filed May 10, 2010, dated Jul. 27, 2016, 4 pgs.
Clark, Kenneth A.; Restriction Requirement for U.S. Appl. No. 14/209,257, filed Mar. 13, 2014, dated Oct. 4, 2016, 7 pgs.
Gifford, Paul; International Search Report and Written Opinion for PCT Application No. PCT/US16/36007, filed Jun. 6, 2016, dated Oct. 6, 2016, 12 pgs.
Hyland, Gregory E.; Notice of Allowance for U.S. Appl. No. 14/450,452, filed Aug. 4, 2014, dated Jun. 15, 2017, 17 pgs.
Hyland, Gregory E.; Canadian Office Action for Serial No. 2,741,843, filed Oct. 27, 2009, dated Apr. 25, 2017, 7 pgs.
Clark, Kenneth A.; Final Office Action for U.S. Appl. No. 14/209,257, filed Mar. 13, 2014, dated Jun. 28, 2017, 41 pgs.
Clark, Kenneth A.; Office Action for Australian Application No. 2014235054, filed Mar. 13, 2014, dated Jun. 2, 2017, 3 pgs.
Hyland, Gregory E.; European Search Report for serial No. EP2433440, filed Nov. 18, 2011,, dated Apr. 10, 2017, 6 pgs.
Clark, Kenneth A.; Office Action for Mexico Application No. MX/a/2015/011793, filed Mar. 13, 2014, dated Feb. 20, 2017, 7 pgs.
Hyland, Gregory E.; Non-final Office Action for U.S. Appl. No. 14/450,452, filed Aug. 4, 2014, dated Feb. 2, 2017, 40 pgs.
Hyland, Gregory E.; Corrected Notice of Allowability for U.S. Appl. No. 14/450,452, filed Aug. 4, 2014, dated Jul. 18, 2017, 6 pgs.
Hyland, Gregory; Corrected Notice of Allowability for U.S. Appl. No. 14/450,452, filed Aug. 4, 2014, dated Sep. 26, 2017, 4 pgs.
Hyland, Gregory E.; Office Action for Canadian patent application No. 2,772,545, filed May 20, 2010, dated Jun. 22, 2017, 3 pgs.
Clark, Kenneth A.; Applicant-Initiated Interview Summary for U.S. Appl. No. 14/209,257, filed Mar. 13, 2014, dated Jul. 19, 2017, 7 pgs.
Clark, Kenneth A.; Office Action for Mexico Application No. MX/a/2015/011793, filed Mar. 13, 2014, dated Jun. 20, 2017, 8 pgs.
Hyland, Gregory; Issue Notification for U.S. Appl. No. 14/450,452, filed Aug. 4, 2014, dated Oct. 4, 2017, 1 pg.
Clark, Kenneth A.; Non-Final Office Action for U.S. Appl. No. 14/209,257, filed Mar. 13, 2014, dated Oct. 16, 2017, 33 pgs.
Clark, Kenneth A.; Non-Final Office Action for U.S. Appl. No. 15/347,849, filed Nov. 10, 2016, dated Nov. 3, 2017, 84 pgs.
Gifford, Paul; Non-Final Office Action for U.S. Appl. No. 15/171,722, filed Jun. 2, 2016, dated Oct. 16, 2017, 76 pgs.
Gifford, Paul; Non-Final Office Action for U.S. Appl. No. 15/171,722, filed Jun. 2, 2016, dated Nov. 17, 2017, 90 pgs.
Gifford, Paul; Notification Concerning International Preliminary Report on Patentability for PCT Application No. PCT/US16/36007, filed Jun. 6, 2016, dated Dec. 14, 2017, 9 pgs.

* cited by examiner

INFRASTRUCTURE MONITORING SYSTEM AND METHOD

CROSS-REFERENCE TO RELATED APPLICATIONS

This application is a continuation of U.S. patent application Ser. No. 12/606,957 filed on Oct. 27, 2009, which claims the benefit of U.S. Provisional Application No. 61/108,770, filed Oct. 27, 2008, and U.S. Provisional Application No. 61/180,600 filed May 22, 2009, the entire disclosures of which are hereby specifically and entirely incorporated by reference.

BACKGROUND

1. Field of the Invention

The invention is directed systems and methods of monitoring and controlling an infrastructure such as, but not limited to the supply and use of commercial, industrial or residential water, gas and/or electric, and, in particular, to methods and systems for monitoring and controlling a municipality and alerting a user to potential faults.

2. Background of the Invention

Municipalities administer and/or outsource numerous safety systems within each municipality. Such systems are usually complex infrastructures and include but are not limited to water distribution, gas distribution, electricity distribution, waste management, traffic control, fire departments, police departments, and emergency response departments. Each of these systems needs to be monitored for use (authorized or unauthorized), faults, tampering, events, leaks, contamination, and/or other issues.

Often to obtain an understanding of the state of any one system, or for billing or repair purposes, personnel must be sent into the municipality to manually check for problems within the system. This is slow, labor-intensive process can lead to overlooked problems. Furthermore, preferred aspects of the system may only be evaluated irregularly or infrequently, thereby allowing a problem to go unchecked for long periods of time. For example, a leak in a water main may cost a water company a significant amount of money in lost water, energy usage, and chemical treatment, particularly if the leak is not discovered for a long period of time. Furthermore, a leak can lead to underground structural erosion.

Another problem and disadvantage associated with current systems is the lack of property rights sufficient to maintain a network of monitors and device controllers capable of creating a transmission infrastructure that can adapt to multiple monitors and controllers and form an information network for providing information about the system to the utility monitoring the network. For example, some networks require new polls or towers to be erected for placement of the communication devices.

Furthermore, an issue in one system may cause an issue in another system. For example, a fire reported to the fire department may require the gas company to shut off gas flow to the vicinity of the fire and require the water company to redirect water or additional water pressure to the vicinity. However, current systems are not interoperable. Therefore, it is desirable to have a single system that can monitor different aspects of at least one municipality system continuously and communicate with several entities at the same time.

SUMMARY OF THE INVENTION

The present invention overcomes the problems and disadvantages associated with current strategies and systems and provides new systems and methods of monitoring municipality infrastructure.

One embodiment of the invention is directed to an infrastructure monitoring system. The system includes an operations center, and a number of monitoring devices in communication with the operations center. Each monitoring device has at least one sensor sensing at least one condition within an infrastructure, a data storage device storing data sensed by the sensors, a communications device to transmit and receive data, and a processor in communication with a sensor, the data storage device, and/or the communications device. At least one monitoring device monitors a first aspect of the infrastructure and at least one monitoring device of monitors a second aspect of the infrastructure.

In preferred embodiments, the operations center and the monitoring devices are in wireless communication. In other embodiments, at least one output device is in communication with the operations center. Each output device has a communications device to receive and/or transmit data, at least one output port, and a processor in communication with the communications device and/or the at least one output port.

In preferred embodiments, the operations center and at least one output device are in wireless communication. Each monitoring device and each output, device can be adapted to receive transmissions for a second monitoring device or output device and retransmit the transmission to the second monitoring device or monitoring device. Additionally, each monitoring device and each output device can be adapted to receive transmissions for the operations center and retransmit the transmission to the operations center.

In preferred embodiments, at least one output device is connected to an actuator control device, an alarm, a Radio-Frequency Identification device and/or a tamper prevention device. In preferred embodiments, a monitoring device and an output device are contained within the same unit. In such embodiments, the monitoring device and the output device can share a power source, a communications device, and/or a processor.

In preferred embodiments, the infrastructure is at least one of a water distribution system, an electricity distribution system, a gas distribution system, a traffic control system, and an emergency response system. In preferred embodiments, the monitoring device can monitor for at least one of use of a commodity, tampering, leaks, GPS location, proximity, tilt, smoke, temperature, rust, corrosion, fluid flow, pressure, water quality, air quality, and motion. The system can produce an alert when the at least one monitoring device registers an event. The monitoring device can be coupled to a camera.

In preferred embodiments, there are multiple operations centers. Each operations center can be uniquely located. Each operations center monitors a number of infrastructures concurrently. The infrastructures of are selected from the group including water systems, electrical systems, gas systems, emergency response systems, traffic control systems, and combinations thereof.

Another embodiment of the invention is directed to a method of disseminating information. The method includes the steps of obtaining information about at least one infrastructure from an infrastructure monitoring system, evaluating the information, and disseminating the information. The infrastructure monitoring system includes an operations center and a number of monitoring devices in communication with the operations center. Each monitoring device has at least one sensor sensing at least one condition within the infrastructure, a data storage device storing data sensed by the sensor, a communications device to transmit and receive data, and a processor in communication with the sensor, the data storage device, and/or the communications device. At least one monitoring device monitors a first aspect of the infrastructure and at least one monitoring device monitors a second aspect of the infrastructure.

In preferred embodiments, the information is disseminated to at least one of an emergency responder, a utility repair crew, and a dispatcher. The information can be disseminated to two or more entities. In preferred embodiments, the information obtained relates to at least one of commodity use, tampering, leaks, location, proximity, tilt, smoke, temperature, rust, corrosion, fluid flow, pressure, water quality, air quality, and motion.

In preferred embodiments, the infrastructure is selected from the group consisting of water systems, electrical systems, gas systems, emergency response systems, traffic control systems, and combinations thereof. The information can be obtained from a number of infrastructures concurrently. In the preferred embodiment, the information is transmitted over a wireless network. The wireless network is preferably a telecommunications network and the information is disseminated to at least one portable device.

In the preferred embodiment, the information is evaluated to determine if an aspect of the infrastructure exceeds a predetermined threshold. In the preferred embodiment, information is transmitted from the at least one sensor to the operations center.

Other embodiments and advantages of the invention are set forth in part in the description, which follows, and in part, may be obvious from this description, or may be learned from the practice of the invention.

DESCRIPTION OF THE DRAWINGS

The invention is described in greater detail by way of example only and with reference to the attached drawings, in which.

DETAILED DESCRIPTION

Figure 1:
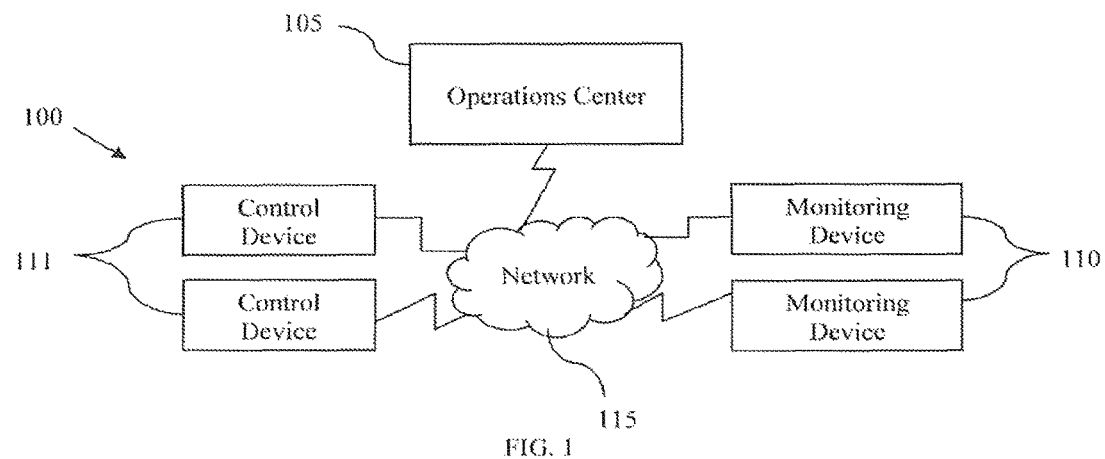
FIG. 1 is a schematic of one embodiment of the system of the invention.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

A problem in the art capable of being solved by the embodiments of the present invention is monitoring and maintaining an infrastructure. It has surprisingly been discovered that monitoring devices with one or two way communication abilities can be used to detect faults in the municipality's systems and provide on-demand, real time, or near real time device status, maintenance, and control over the systems.

A network of monitoring devices of the invention is capable of providing a system administrator with a full picture of the current state of the system. The network preferably includes an array of different monitoring devices each capable of sensing at least one condition. The monitoring devices may be capable of sending and receiving data to and from at least one operations center. Communication may be from the remote monitoring device to a central monitoring facility, to one of a number of regional monitoring centers, to a user, and/or to a research facility. Furthermore, the system preferably includes at least one control device. Each control device is adapted to control a different aspect of the system. The control devices may be part of the monitoring devices or may be separate units. Communication is preferably over the Internet, but may be over a private network, a local area network, or a wide area network. Preferably the communication involves a wireless component, such as from the remote monitoring device and/or control device to a regional monitoring facility, or to distributed monitors. Also preferably, the communications are secured or encrypted such that the communications system cannot be monitored by another unknown party. Preferably access to the system is granted through user names and passwords, although additional and/or alternate encryption methods can be employed.

One embodiment of the invention is directed to water infrastructure systems. In such systems, monitoring devices can be located throughout the system, for example, as attachments to component parts, for feedback to a network that can provide real-time information to the utility operating the network. The network operators can use the information transmitted to activate controlling devices on the network, or to dispatch repair or other services as directed by the information provided by the network. For example, if water pressure monitors on a water meter indicate a variance between locations, a water leak can be reported using the network, and controlling devices can divert water. Pressure meters can be attached to fire hydrants to monitor and report pressure losses throughout the system, providing real-time information to benefit the users of the fire hydrants (fire departments who need to be assured of adequate pressure), the users of the system (water consumers who will be affected by lower pressure), and the operators of the system (who suffer asset loss as a result, of lack of real-time information about losses).

FIG. 1 depicts a system 100 of the invention for monitoring, controlling, and communicating with at least one monitoring device and/or at least one control device. System 100 includes an operations center 105 in communication with at least one monitoring device 110 and/or one control device 111. In the preferred embodiment, there is bi-directional communication between operations center 105 and devices 110 and 111. Communications can be simplex or duplex. Communication can occur over any communications network 115 known in the art, including but not limited to wired networks, wireless networks, Zigbee networks, Bluetooth networks, Z-wave networks, WiFi networks, WiMax networks, RF networks, local area networks (LAN), internet networks, wide area networks (WAN), cellular telephone network, hardwired telephone networks, 900 MHz wireless networks, and satellite networks. In the preferred embodiment, the network is a fixed network. For example, the fixed network can be a mesh network or a star network. Additionally, devices 110 and 111 and operations center 105 can be in direct communication or can communicate through an intermediary device, such as a relay or a gateway.

Each monitoring device 110 of the invention preferably monitors at least one aspect of the infrastructure. The monitored aspect can be one or more of the components of the infrastructure (e.g. pipe conditions, valve conditions, fire hydrant conditions, service line conditions, meter conditions, power line conditions, and battery conditions), commodity conditions (e.g. fluid or gas flow, fluid or gas pressure, fluid or gas temperature, and fluid or gas contaminants), or combinations thereof. Additionally, the monitors can be self monitoring. For example the monitors preferably determine if there is a loss of communication, low battery levels, and/or internal damage (e.g. short circuits due to water damage). Additionally, each monitoring device 110 can be structurally stable (e.g. fixed to a valve, pipe, or meter) or movable (e.g. allowed to move with or within the flow of water or gas in the pipes).

Each node in the network of the invention preferably detects errors in transmissions. Error detection can use cyclic redundancy codes using a tabled based on a defined polynomial or any other method of error detection. In preferred embodiments, transmissions can be rerouted if the primary route is blocked or otherwise unavailable. Furthermore, devices 110 and 111 can confirm receipt of a message, e.g. via a hand shake protocol. In instances where confirmation is not received the message can be resent along the same rout or rerouted.

In preferred embodiments, each monitoring device 110 and each control device 111 is assigned a unique identifier. The unique identifier can be related to the devices' geographical locations, street addresses, order of installation, or any other method of identifying the devices. Furthermore, different types of devices 110 and 111 can have identifiers that are unique to that type of device. For example, the identifier for all water meters can start with a WM, while the identifier for all leak detectors can start with a LD. Each communication to and from a device 110 and 111 can include the unique identifier so that the message is received by the correct device 110 or 111, or operations center 105 can determine where the message was sent from.

Each monitoring device 110 and each control device 111 can be retrofitted to an existing system or device, can be coupled to a new system or device, or can be integrated into a new system or device. For example, the system can be connected to, work with, or work independently of a Supervisory control and data acquisition (SCADA) network. In preferred embodiments, each monitoring device 110 and each control device 111 has a set of adapters to facilitate coupling the monitoring device 110 or control device 111 to a new or existing system or device.

In preferred embodiments, system 100 is divided into sectors with each sector having at least one monitoring device 110 and/or at least one control device 111. Each sector can communicate directly with operations center 105 or each sector can have at least one intermediary communications device that is in communication with the monitoring device 110 and/or control device 111 and operations center 105. In the preferred embodiment, the sectors are divided up by geographical location. For example, all of the devices in one neighborhood can be in a single sector and there is one sector for each neighborhood. In preferred embodiments, one intermediary communications device can service multiple sectors.

In preferred embodiments, each monitoring device 110 and/or control device 111 can communicate with adjacent monitoring devices 110 and/or control devices 111. In such embodiments, each device 110 and/or 111 can act as a transceiver or relay by receiving messages intended for another device or for the operations center 105 and forwarding the message. In embodiments where the system 100 is divided into sectors, monitoring devices 110 and control devices 111 can only communicate within their sector. In other embodiments, monitoring device 110 and control device 111 can communicate with devices 110 and/or 111 in other sectors. Each remote monitoring device 110 and/or the operations center 105 may be able to determine if a transmitted message was received by the intended device and, if not, may be able to reroute the message until the message is properly received. Additionally, relay devices can be implemented in the system to further extend the range of communications. For example, relay devices can be placed on telephone poles, on municipal buildings, within fire hydrants, and/or under manhole covers. In preferred embodiments, devices 110 and 111 communicate over a mesh network. In the mesh network, devices 110 and 111 can communicate with other devices 110 and 111 within the mesh network. Operations center 105 can set specified communications pathways derived from routing tables.

Operations center 105 can be located at a municipality office, a private or public company, a fire station, a police station, or any other entity that monitors operations center 105. In other embodiments, operations center 105 can be a remotely hosted operations center accessible by a device capable of accessing the Internet. In such embodiments, operations center 105 can take advantage of cloud computing (e.g. a network of remotely hosted computers, servers, and data storage devices). Compared to non-remotely hosted computer networks, cloud computing can increase ease of use, increase access, increase security, decrease costs, be custom tailored, and provide an unrestricted expansion of storage space. Additionally, in preferred embodiments, there is a plurality of operations centers 105. One or more operations centers can be located at different entities and each control center can monitor a different aspect of system 100. For example, in embodiments where one monitoring device monitors water usage and another monitors gas leaks, the water usage aspect can be monitored by a water utility company and the gas leaks can be monitored by the gas utility company and/or the fire department. In preferred embodiments, there are redundant operations centers 105, where at least two operations centers 105 monitor the same aspect of system 100. Operations center 105, in preferred embodiments, can send transmissions to update the firmware of devices 110 and 111.

Figure 2:
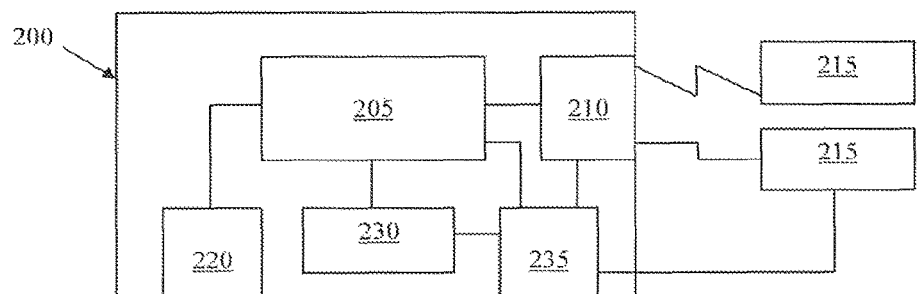
FIG. 2 is a schematic of one embodiment of the monitoring device of the invention.

FIG. 2 is a schematic of a monitoring device unit 200. Monitoring device unit 200 includes a processor 205. Processor 205 is coupled to at least one input port 210 for receiving data from sensors 215. Processor 205 is also coupled to a transceiver 220 for sending and receiving signals. In preferred embodiments, processor 205 is coupled to a data storage unit 230. Data storage unit 230 can hold a predetermined amount of data received from the sensors 215. For example, data storage unit 230 can hold data for a predetermined amount of time (e.g. one day, one week, or one month), can hold a predetermined number of readings (e.g. 10 readings, 100 readings, 1000 readings), or can hold data until directed to purge the data by the operations center. Additionally, data storage unit 230 can hold instructions for processor 205 to execute upon prompting from the operations center. In the preferred embodiments, processor 205 compiles at least some of the data stored in data storage unit 230 for transmitting to the operations center.

Each remote monitoring device 200 may collect data and/or transmit data continuously, at specific intervals, or randomly. In embodiments where the monitoring device 200 collects and transmits data in a non-continuous configuration, monitoring device 200 may turn off or reduce power consumption during the non-data collecting periods to save energy. In preferred embodiments, processor 205 is coupled to a power source 235. Power source 235 can be a device capable of powering processor 205 and devices attached to processor 205. For example, power source 235 can be a battery, solar panel array, wind turbine, water turbine, electrical lines, or combinations thereof. In preferred embodiments, there is also a backup power source, such as a battery. In preferred embodiments, the power may derive from the operation of the infrastructure system.

In the preferred embodiment, processor 205 is coupled to at least one sensor 215 that monitors at least one condition associated with the monitoring device. In preferred embodiments, sensors 215 can determine the status of a device. Sensors 215 can be directly wired to processor 205 or can use wireless communication to send and receive signals from processor 205. Sensors 215 can be positioned within the monitoring device or be external to the monitoring device. In preferred embodiments, sensors 215 are positioned remote from the monitoring device. For example a sensor can be positioned on a nearby building or telephone pole. In the embodiments, where sensors 215 and processor 205 communicate wirelessly, the same communications protocol can be used in the sensor/processor communication as in the processor/operations center communication, or different communications protocols can be used in the sensor/processor communication as in the processor/control center communication. For example, the sensor/processor communications can use RF protocols while the processor/control center communications can be over a wired network.

In preferred embodiments, sensor 215 is a use monitor. In such embodiments, the use monitor records the amount of water, gas, electricity, or other commodity that is used by a customer over a specified period of time. The use monitor can continuously record the amount of the commodity used or the use monitor can provide a signal to processor 205 that the commodity is in use. Processor 205 can transmit a signal to the operations control to alert the operations center that the monitoring device is being used and/or how much of the commodity is flowing through the sensor. In preferred embodiments, the operations center can request a reading from the use monitor on demand. In preferred embodiments, the processor or the operations center can determine based on the use, if there is unauthorized use of the commodity. Upon detection of unauthorized use, at least one of processor 205 or the operations center can generate an alarm that there is unauthorized use. For example, in embodiments where the use monitor is coupled to a fire hydrant, if the use monitor indicates that the fire hydrant is in use, however no fire is reported, the operations center can disseminate an alert that there is potential misuse of the fire hydrant.

In preferred embodiments, at least one sensor 215 is a tamper sensor. The tamper sensor can be a motion detector, a contact sensor, a rotation sensor, a touch sensor, a proximity sensor, a biofeedback sensor, a temperature sensor, a capacitance sensor, a resistance sensor, or any other sensor that is able to detect the presence of an object. The tamper sensor can send a message to processor 205 when the tamper sensor detects an event. The processor 205 will then evaluate the event to determine if a device being monitored is being tampered with or will relay the message to the operations center for evaluation. The monitored device can be a fire hydrant, utility meter, valve, manhole cover, pump, or any other device that may be tampered with. Upon detection of a tamper event, at least one of processor 205 and the operations center can generate an alarm that the device is being tampered with. In preferred embodiments, the monitoring device may activate a tamper prevention device (described below). In preferred embodiments, the operations center will send a transmission to processor 205 telling processor 205 to disregard messages from the tamper sensor for a predetermined period of time or until another message is received from the operations center telling processor 205 to resume monitoring for tamper events. For example, if a fire department needs to use a fire hydrant, the operations center will send a message to processor 205 to temporarily disregard any tamper events. Once the fire department is finished using the fire hydrant the operations center will send a message to processor 205 to start monitoring for tamper events again.

In preferred embodiments at least two of sensors 215 are leak detectors. Each leak detector can include an in-pipe leak detector and/or an exterior leak detector. In gas applications, the leak detectors are preferably vapor sensors. While in liquid applications, preferably the leak detectors use acoustic monitoring to determine presence and location of a leak. The energy generated from a leak is transmitted within a pipe through the commodity as well as through the pipe wall. Each leak detector can detect the vibrations made by the leak in the commodity or the pipe wall, joint or service line. To determine the location of a leak, at least two detectors must detect the same leak. Based on the velocity of the sound traveling along the pipe (V), the distance between the two detectors (D) and the delay between the times each detector detects the sound (T), the location of the leak (L) can be determined by the following equation:

$$L=(D-(V \times T))/2$$

When using the above equation, the typical velocity of sound in water is about 1500 m/s while the typical speed of sound through an iron pipe is 5100 m/s. The velocity can be measured empirically. For example, if the leak is exactly midway between the two detectors the sound would reach both detectors at the same time. Each detector may monitor continuously or at predetermined periods of time. The leak detectors can send a message to processor 205 when the leak detectors detect an event. The processor 205 can then evaluate the event to determine if there is a leak and how severe the leak is or can relay the message to the operations center for evaluation. Upon detection of a leak event, at least one of processor 205 or the operations center can generate an alert that there is a leak if the leak is determined to be severe enough to warrant attention.

In preferred embodiments, at least one sensor 215 is a smoke detector. The smoke detector can be a photoelectric detector, an ionization detector, or any other device that can detect the presence of smoke. The smoke detector can be located within the monitoring device or exterior to the monitoring device. In the preferred embodiment, the smoke detector monitors continuously for smoke. The smoke detector can send a message to processor 205 when the smoke detector detects an event. The processor 205 can then evaluate the event to determine if there is smoke or can relay the message to the operations center for evaluation. Upon detection of smoke, at least one of processor 205 or the operations center can generate an alert that there is smoke.

In preferred embodiments, at least one sensor 215 is a temperature sensor. The temperature sensor can be a contact sensor (e.g. thermocouples, thermistors, liquid-in-glass thermometers, resistance temperature detectors, filled system thermometers, bimetallic thermometers, semiconductor temperature sensors, and phase change indicators) or a non-contact sensor (e.g. radiation thermometers, thermal imagers, ratio thermometers, optical pyrometers, and fiber optic thermometers). The temperature sensor can be located within the monitoring device or exterior to the monitoring device. In the preferred embodiment, the temperature sensor monitors continuously for the temperature to rise above or drop below a predetermined threshold. The temperature sensor can send a message to processor 205 when the temperature sensor detects a temperature beyond the thresholds. The processor 205 can then evaluate the event to determine if there the temperature is a problem (such as freezing pipes or fire) or can relay the message to the operations center for evaluation. Upon detection of undesirable temperatures, at least one of processor 205 or the operations center can generate an alert that there is an undesirable temperature condition.

In preferred embodiments, at least one sensor 215 is a rust and/or corrosion sensor. The sensor can detect rust and/or corrosion using any method known in the art, including but not limited to liquid penetration inspection, magnetic particle inspection, radiographic inspection, visual inspection, eddy current inspection, ultrasonic inspection, and thermographic inspection. The sensor can send a message to processor 205 when the sensor detects a rust or corrosion beyond a threshold value. The processor 205 can then evaluate the rust or corrosion to determine if there is a problem or can relay the message to the operations center for evaluation. Upon detection of undesirable rust or corrosion, at least one of processor 205 or the operations center can generate an alert that there is an undesirable amount of rust or corrosion.

In preferred embodiments, at least one sensor 215 is a fluid flow sensor. Fluid flow sensor can be used either in gas systems or liquid systems. The fluid flow sensor can detect direction of the flow, turbidity of the flow, velocity of the flow, density of the flow, viscosity of the flow, and/or any other aspect of the flow. The fluid flow sensor may be a velocimeter, a laser-based interferometer, a vane, a rotary potentiometer, a Hall effect sensor, a device to measure heat transfer caused by the flowing fluid, or any other device know in the art to measure the flow of fluid. The sensor can send a message to processor 205 when the sensor detects a flow anomaly. The processor 205 can then evaluate the event to determine if the anomaly is a problem or can relay the message to the operations center for evaluation. Upon detection of an anomaly, at least one of processor 205 and the operations center can generate an alert that there is an anomaly.

In preferred embodiments, at least one sensor 215 is a pressure sensor. In the preferred embodiment, the pressure sensor is positioned within the flow of fluid or area in which the pressure is being sensed. For example, the pressure sensor can be positioned at the base of a fire hydrant and in the water to determine the water pressure within water system, in a pipe to determine gas or water pressure within a gas or water system, or in a room to determine air pressure within the room. The pressure sensor can be a piezoresistive strain gauge, a capacitive gauge, an electromagnetic gauge, a piezoelectric device, or any other device know in the art to measure pressure. The sensor can send a message to processor 205 when the sensor detects a pressure anomaly. The processor 205 can then evaluate the event to determine if the anomaly is a problem or can relay the message to the operations center for evaluation. Upon detection of an anomaly, at least one of processor 205 or the operations center can generate an alert that there is an anomaly.

In preferred embodiments, at least one sensor 215 is a water quality monitor. The water quality monitor can monitor a single aspect of water flowing through the system or multiple aspects of the water. For example, the water quality monitor can monitor one or more of the water's bacteria levels, pharmaceutical levels, alkalinity, chlorine and/or chloramine levels, hardness, pH levels, peroxide content, iron levels, nitrate levels, nitrite levels, arsenic levels, pollution levels, oxygen levels, biomass levels, and/or any of the other contaminants regulated by the Environmental Protection Agency (EPA), in embodiments where there are multiple monitoring devices, all the devices can monitor the same aspects, each device can monitor a different aspect, or a combination thereof. In the preferred embodiment, the water quality monitors test the water continuously, however, in preferred embodiments, the water quality monitors test the water at predetermined time intervals (e.g. once, a hour, once a day, once a week, etc.). Each water qualify monitor relays data to processor 205. Processor 205 can store the data on database 230 or transmit the data to the operations center. Either processor 205 or the operations center can monitor the data received from the water quality monitors to determine if there is a change in the levels of the contaminants or if the levels of the contaminants rise above a threshold, level, Upon detection of unsafe contamination levels, at least one of processor 205 or the operations center can generate an alert that there is contamination in the water system.

In the embodiments where at least two monitoring devices are monitoring the same aspect of the water, the operations center can determine if there is a change in the aspect of the water from the location of one monitoring device to the location of the other. If there is a change, the operations center can generate an alert that there is a change in the water system and output the approximate location of the change in the aspect of the water.

In preferred embodiments, at least one sensor 215 is an air quality monitor. The air quality monitor can monitor a single aspect of the air or multiple aspects of the air. Furthermore, the air quality monitor can monitor the air within a facility or ambient air. For example, the air quality monitor can monitor one or more of the air's benzene levels, carbon disulfide levels, urethane levels, formaldehyde levels, phosphorus levels, naphthalene levels, parathion levels, quinoline levels, trifluxalin levels, and/or any of the other contaminants whose acceptable levels have been set by the Environmental Protection Agency. In embodiments were there are multiple monitoring devices, all the devices can monitor the same aspects or each device can monitor a different aspect, or a combination thereof. In the preferred embodiment, the air quality monitors test the air continuously, however, in preferred embodiments, the air quality monitors test the air at predetermined time intervals (e.g. once a hour, once a day, once a week, etc.). Each air quality monitor relays data to processor 205. Processor 205 can store the data on database 230 or transmit the data to the operations center. Either processor 205 or the operations center can monitor the data received from the air quality monitors to determine if there is a change in the levels of the contaminants or if the levels of the contaminants rise above a threshold level. Upon detection of unsafe contamination levels, at least one of processor 205 or the operations center can generate an alert that there is contamination in the air.

In the embodiments where at least two monitoring devices are monitoring the same aspect of the air, the operations center can determine if there is a change in the aspect of the air from the location of one monitoring device to the location of the other. If there is a change, the operations center can generate an alert that there is a change in the air and output the approximate location of the change in the aspect of the air. Furthermore, in embodiments where there is a time stamp associated with each reading, the control center can determine the approximate direction and speed at which the contaminant is moving.

In preferred embodiments, at least one sensor 215 is a motion detector. The motion detector can be a radar-based motion detector, a photo-sensor motion detector, a passive infrared motion detector, a magnetic motion detector, a pressure sensitive motion detector, or any other device capable of detection the motion of objects. The motion detector can be used, for example, to count the number of cars passing through an intersection to control a traffic light, for tamper prevention as described above, for security purposes, and/or to control street lights. The motion detector can be placed within the monitoring device or exterior to the monitoring device. Upon detecting motion, the motion detector can relay the detection to processor 205. Processor 205 can save the detection on database 230 or transmit a message regarding the detection to the operations center. Processor 205 or the operations center can evaluative the detection and act in accordance with the purpose of the motion detector. For example, if the motion detector detects a predetermined number of vehicles have passed the monitoring device, processor 205 or the operations center can cause a traffic light to switch from green to red. As a second example, if the motion detector detects a motion after a predetermined time, e.g. after sunset, processor 205 or the operations center can cause the street lights near the monitoring device to illuminate for a predetermined period of time.

In preferred embodiments, at least one sensor 215 is a tiltmeter. The tiltmeter can be a pendulum, a water tube, a bubble-level meter, and/or a MEMS electronic meter. The tiltmeter can be located on devices within the system, such as, but not limited to, pipes, fire hydrants, meters, valves, telephone poles, manhole covers, and light posts. The sensor can send a message to processor 205 when the sensor detects a tilt beyond a threshold value. The processor 205 can then evaluate the tilt to determine if there is a problem or can relay the message to the operations center for evaluation. Upon detection of undesirable tilt, at least one of processor 205 or the operations center can generate an alert that there is an undesirable tilt. For example, if a telephone pole is struck by a car, the tiltmeter will indicate that the telephone pole is tilting at an undesirable level and the operations center can alert the municipality to send out a repair crew to assess the situation and repair the telephone pole.

In preferred embodiments, at least one sensor 215 is a proximity sensor. The proximity sensor can use electromagnetic technology, electrostatic technology, infrared technology, or a touch switch. The proximity sensor can detect if devices are properly closed or if devices are improperly touching. The sensor can send a message to processor 205 when the sensor detects proximity beyond a threshold value. The processor 205 can then evaluate the proximity to determine if there is a problem or can relay the message to the operations center for evaluation. Upon detection of undesirable proximity, at least one of processor 205 or the operations center can generate an alert that there is an undesirable proximity. For example, if a valve is improperly closed, the proximity sensor will indicate that the valve is not closed and processor 205 can alert the municipality to take proper actions to close the valve.

In preferred embodiments, at least one sensor 215 is a camera. The camera can be an infrared camera, a video camera, a still camera, a digital camera, a film camera, combinations thereof, or any other device capable of acquiring an image. In a preferred embodiment, the camera is a digital video camera that takes video images continuously. In another preferred embodiment, the camera is a digital still camera that takes still images at regular intervals or upon command from processor 205. In preferred embodiments, the camera can be a traffic camera and take a picture when instructed to by processor 205, for example upon determination that a vehicle is running a red light. In other embodiments, the camera is be use to perform visual inspections of the systems infrastructure. For example, the field of view of the camera can include a device within the system that is apt to corrode and the camera can provide an easy method to visually inspect any degradation of the device. The camera can send image data to processor 205 where the data is stored on database 230 or is transmitted to the operations center. In preferred embodiments, image data is streamed continuously from the camera to processor 205 and from processor 205 to the operations center. The data stream can either be live or delayed. The camera can be located on the monitoring device, near the monitoring device, or within the monitoring device with a portion of the camera extending outside the monitoring device or with a hole in the monitoring device through which the camera can obtain images. In preferred embodiments, the camera is positioned on an actuator. The actuator can move to reposition the field of view of the camera. The actuator can move upon demand from processor 205 or can move autonomously. In the embodiments where the actuator moves autonomously, the movement can be continuous or sporadic.

In preferred embodiments, at least one sensor 215 is a Global Positioning System (GPS) receiver. In the preferred embodiment, the GPS receiver is located on devices within the system, such as, but not limited to, pipes, fire hydrants, meters, valves, telephone poles, manhole covers, and light posts. The sensor can send a message to processor 205 indicating the sensor location. The processor 205 can then relay the message to the operations center for evaluation, conformation, and documenting. Upon detection of unexpected location, at least one of processor 205 or the operations center can generate an alert mat the sensor has moved, possibly indicating that the device has been dislodged, tampered with, or stolen. Additionally, the GPS location can be used, for example, by emergency responders to locate fire hydrants, or repair crews to determine the location of a buried device. In such embodiments, the operations center can disseminate information to the emergency responders or repair crews to easily locate the device. The dissemination can occur by any method, including but not limited to, verbally, over a telecommunications network (e.g. to a smart phone or portable computer), or over a shortwave radio. In embodiments where the monitoring device is moving with the flow of fluid, the sensor can provide updated locations of the monitoring device to track, for example, the flow or contamination levels within the flow.

Other possible sensors 215 connected to monitoring device 200 can include, but are not limited to, flow rate meters, backflow meters, system status monitors, and power level monitors.

Figure 3:
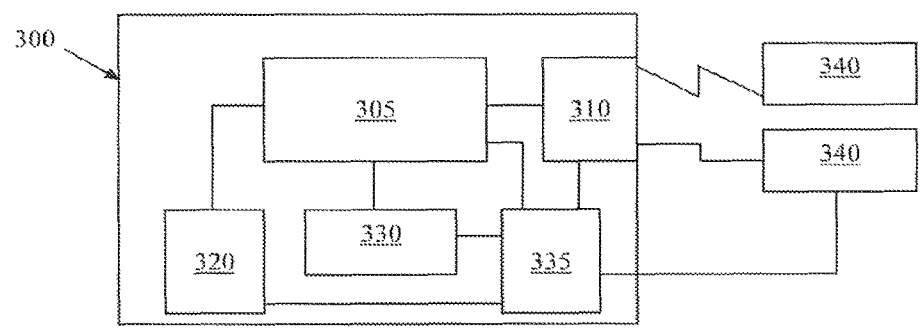
FIG. 3 is a schematic of one embodiment of a control device of the invention.

FIG. 3 is a schematic of a control device 300. Control device 300 includes a processor 305. Processor 305 is coupled to at least one output port 310 for controlling an output device 340. Processor 305 is also coupled to a transceiver 320 for sending and receiving signals. Processor 305 is communicatively coupled to output port 310. Output port 310 is connected to at least one output device 340. Each output device can 340 have the same purpose or each output device 340 can have a different purpose, or combinations thereof. Output devices 340 can be located within control device 300 or external to control device 300, as shown. Furthermore, output devices 340 can be attached to control device 300 or can be remote from control device 300. Output devices 340 communicate with output port 310 through wired or wireless communication channels. In preferred embodiments, output devices 340 are capable of bidirectional communication. In preferred embodiments, control device 300 is an integral part of a monitoring device. In such embodiments, the control device and the monitoring device can share the same processor and/or transceiver.

In preferred embodiments, processor 305 is coupled to a data storage unit 330. Data storage unit 330 may store instructions for processor 305 of how to control output devices 340. In preferred embodiments, processor 305 is coupled to a power source 335. Power source 335 can be any device capable of powering processor 305 and any devices attached to processor 305. For example, power source 335 can be a battery, solar panel array, wind turbine, water turbine, electrical lines, or combinations thereof. In preferred embodiments, there is also a backup power source, such as a battery.

In preferred embodiments, at least one output device 340 is an actuator control device. The actuator control device can control any type of actuator, including but not limited to, a tamper prevention device, a locking device, a camera motion device, a fire hydrant nut opening device, or a valve. The actuator control device can control the actuator autonomously or upon demand from processor 305. For example, upon receiving a signal that a particular event has been sensed, processor 305 may send a command to the actuator control device to act in a particular manner. Likewise, in preferred embodiments the control signal may come from the operations center. The actuator can be mechanical, electrical, or a combination thereof.

In preferred embodiments, at least one output device 340 is an alarm. The alarm can be a visual alarm, an audible alarm, a tactile (i.e. vibration) alarm, or a combination thereof. The alarm can be located within the monitoring device, exterior to the monitoring device, at the operations center, remote from the system, or any other location to alert people. Furthermore, there can be more than one alarm at different locations. For example, in the embodiments where there is a smoke detector, there can be an audible alarm located within the fire detector to alert people around the monitoring device of a potential fire, there can be an audible alarm at the fire station to alert the fire department of the potential fire, and there can be a visual alarm at the gas utility company to indicate that the flow gas in the vicinity of the potential fire should be shut off. In preferred embodiments the alarm is controlled by the processor 305, while in other embodiments the alarm is controlled by the operations center. In preferred embodiments, the alarm has an on/off switch controllable locally.

In preferred embodiments, at least one output device 340 is a tamper prevention device. The tamper prevention device can be a mechanical lock, an alarm, a light, an electrical shock generator, a retaining device, an electrical lock, or any other device capable of preventing tampering. The tamper prevention device may merely deter tampering or may incapacitate a person who is trying to tamper with the device, depending on the level of security. In preferred embodiments the tamper prevention device is controlled by the processor 305, while in other embodiments the tamper prevention device is controlled by the operations center.

In preferred embodiments, at least one output device 340 is a Radio-Frequency Identification (RFID) device. The RFID device can broadcast information about the device it is attached to. For example, the RFID device may broadcast manufacturer information, location information, last service date, device information (e.g. make, model, and/or year), current status (e.g. a valve can broadcast if it is open or closed), etc. In preferred embodiments the RFID device is updateable by the processor 305 or by the operations center. The RFID device can be either an active (e.g. battery powered) or passive (e.g. require an external source to provoke signal transmission) device.

EXAMPLES

A system of the invention is monitoring a water distribution infrastructure. The system is used to automatically control the water pressure within the system. Such a system includes a number of water meters disbursed throughout the infrastructure relaying real time use information to a control center. Upon a determination by the operations center that there is low usage of the system (e.g. at night) based on information received by a predetermined number of the water meters, the operations center causes pumps supplying pressure within the system to reduce or cease pumping. Thereby cutting down on the electricity used by the pumps while maintaining enough pressure throughout the infrastructure to satisfy any water needs. The determination to reduce or cease pumping can be also based on information received from pressure sensors disbursed throughout the infrastructure. For example, if the pressure within the infrastructure exceeds a threshold value, the operations center causes the pumps to reduce or cease pumping.

In another example, the system is used to assist in maintaining the infrastructure. Water pipes and valves are often buried underground making it difficult to locate, assess the status of the devices, and repair them if necessary. Using an example of the above described system, each device is equipped with a monitoring the device. The monitoring device, for example, may monitor for corrosion using a corrosion monitor, geographical location using a GPS receiver, and leaks using a leak detector. Upon detection of corrosion and/or a leak, the monitoring device sends a message to the operations center where the information is analyzed. The operations center is able to make a determination if the corrosion and/or leak is severe enough to warrant fixing, if the corrosion and/or leak should be watched to determine if it worsens, or if the corrosion and/or leak can be ignored. The operations center will also alert a person of the situation for further assessment.

If it is determined that the corrosion and/or leak should be fixed, the operations center disseminates information to a repair crew and redirects water flow away from the device. Such information can include location of the device, based on data received the GPS receiver, problem associated with the device, device information (e.g. make, model, and/or year), etc. The monitoring device can also be equipped with a RFID transmitter, which transmits at least, some of the above information. The repair crew receives the information on a smart phone, a portable computer, or other device capable of receiving such information. Upon completion of the repair, the operations center updates the system to indicate a new last repaired date for the device.

In another Example, the system is monitored by several entities within a municipality at the same time. For example, a fire department, a gas utility, a water utility, an electric utility, and traffic control center all monitor the system concurrently. Upon detection of smoke by a monitoring device, the control center alerts each entity of a potential fire. The location of the potential fire is determined by cross-referencing the ID number of the monitoring device with a lookup table or based on information received from a GPS receiver. The fire department uses the location information to send out emergency response personnel to the vicinity of the potential fire. The gas utility uses the location information to divert or shut off gas flow to the vicinity of the potential fire. The water utility uses the location information to divert water to or increase water pressure in the vicinity of the potential fire as well as determines if any fire hydrants in the vicinity of the potential fire are potentially damaged (e.g. are tilted at an unusual angle, are receiving no or little water pressure, or have been tampered with) based on information received from monitoring devices attached to the fire hydrants. The location of the fire hydrants is determined by cross-referencing the ID number of the monitoring device with a lookup table or based on information received from a GPS receiver. The water utility automatically alerts the fire department as to which fire hydrants to use. The water utility also disables any tamper prevention devices associated with the fire hydrants. The electric utility receives a signal that additional pressure may be needed within the water system and provides an increased electrical load to the water pumps. Additionally, the traffic control center adjusts traffic lights en route from the fire station to the vicinity of the potential fire to assist the fire trucks in arriving quickly and safely.

In another example, the system is used to monitor contamination of the fluid flowing through the system. The system includes pressure sensors, leak detectors and contamination detectors. Leaks within the system can cause a pressure drop throughout the system which can lead to contaminants being drawn into the system. For example, if a pipe is under water and the pressure inside the pipe drops below the pressure outside the pipe, the exterior water will flow into the pipe. Therefore, the system has several monitoring devices to check for such potential or actual contamination. The pressure sensors will indicate if the pressure within the system drops below a threshold level at which contaminants can be drawn into the system. The leak detectors will indicate that there is a leak through which contaminants can enter the system. While the contamination detectors will indicate if there is contamination within the system, indicating a possible breach of the infrastructure of the system.

Other embodiments and uses of the invention will be apparent to those skilled in the art from consideration of the specification and practice of the invention disclosed herein. All references cited herein, including ail publications, U.S. and foreign patents and patent applications, are specifically and entirely incorporated by reference. It is intended that the specification and examples be considered exemplary only with the true scope and spirit of the invention indicated by the following claims, furthermore, the term "comprising of" includes the terms "consisting of" and "consisting essentially of." All examples illustrate embodiments of the invention, but should not be viewed as limiting the scope of the invention.

The invention claimed is:

1. An infrastructure monitoring system comprising:
   a first monitoring device configured to
      detect and monitor at least a first condition of a first aspect of an infrastructure, and
      transmit a data signal including data relating to the first condition and a first time stamp;
   a second monitoring device configured to
      detect and monitor the first condition of the first aspect,
      detect and monitor a second condition of a second aspect of the infrastructure, and
      transmit a data signal including data relating to the second condition and data relating to the first condition comprising a second time stamp;
   a third monitoring device configured to
      detect and monitor at least a third condition of a third aspect of the infrastructure, and
      transmit a data signal including data relating to the third condition; and
   an operations center communicatively coupled to each monitoring device, the operations center configured to
      receive the data signal from each monitoring device,
      determine whether the data included in the data signal received from any one of the monitoring devices indicates a problem of at least one of contamination and corrosion within the infrastructure,
      subsequent to the determination of the indication of the problem of corrosion, determine a level of severity of the corrosion and whether the corrosion is severe enough to warrant fixing based on the level of severity of the corrosion, and
      subsequent to the determination of the indication of the problem of contamination, determine an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device;
   wherein the first aspect, the second aspect, and the third aspect define corrosion, contamination, and another different aspect of the infrastructure.

2. The system of claim 1, wherein each monitoring device is wirelessly communicatively coupled to the operations center.

3. The system of claim 1, wherein each monitoring device comprises
   at least one sensor sensing at least one condition of the first, second, and third conditions within the infrastructure,
   a data storage device storing data sensed by the at least one sensor,
   a first communications device adapted to transmit and receive data, and
   a first processor communicatively coupled to the at least one sensor, the data storage device, and the first communications device.

4. The system of claim 3, the infrastructure monitoring system further comprising a control device communicatively coupled to the operations center, the control device comprising
   a second communications device adapted to receive and transmit data,
   at least one output port, and
   a second processor communicatively coupled to the second communications device and the at least one output port.

5. The system of claim 1, wherein an additional condition is related to a leakage aspect of the infrastructure, and another additional condition is related to a pressure aspect of the infrastructure.

6. The system of claim 1, wherein each monitoring device monitors at least one additional condition.

7. The system of claim 1, wherein the infrastructure monitoring system disseminates information about the infrastructure from the infrastructure monitoring system including disseminating an indicia of the problem within the infrastructure.

8. The system of claim 1, wherein the operations center monitors a plurality of infrastructures concurrently.

9. The system of claim 1, wherein the operations center comprises multiple operations centers, and wherein each operation center is located at a different location within the system.

10. A method of disseminating information, the method comprising:
    detecting, by a first monitoring device, a first condition of a first aspect of an infrastructure and transmitting a data signal to an operations center, the data signal including data relating to the first condition and a first time stamp;
    detecting, by a second monitoring device, the first condition of the first aspect and a second condition of a second aspect of the infrastructure, and transmitting a data signal to the operations center, the data signal including data relating to the second condition and data relating to the first condition, and the data signal comprising a second time stamp;
    detecting, by a third monitoring device, a third condition of a third aspect of the infrastructure and transmitting a data signal to the operations center, the data signal including data relating to the third condition;
    determining, by the operations center, whether the data included in the data signal received from any of the monitoring devices indicates a problem of contamination within the infrastructure;
    subsequent to the determination of the indication of the problem of contamination, determining, by the operations center, an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device;
    determining, by the operations center, whether the data included within the data signal received from any of the monitoring devices indicates a problem of corrosion within the infrastructure; and
    subsequent to determination of the indication of the problem of corrosion, determining by the operations center an amount of corrosion determined to be the problem within the infrastructure and a level of severity of the corrosion;
    wherein the first aspect, the second aspect, and the third aspect define different aspects of the infrastructure.

11. The method of claim 10, wherein each monitoring device comprises:
    at least one sensor sensing at least one of the first, second, and third conditions within the infrastructure,
    a data storage device storing data sensed by the at least one sensor,
    a first communications device adapted to transmit and receive data, and
    a first processor communicatively coupled to the at least one sensor, the data storage device, and the first communications device.

12. The method of claim 10, wherein the second monitoring device monitors the first condition.

13. The method of claim 12, further comprising determining, by the operations center, whether a change in data between data as detected by the first monitoring device relating to the first condition from data as detected by the second monitoring device relating to the first condition indicates a second problem within the infrastructure.

14. An infrastructure monitoring system comprising:
    a first monitoring device at a first location, the first monitoring device configured to
        detect and monitor a condition of an aspect of an infrastructure, and
        transmit a data signal including data relating to the condition and a first time stamp;
    a second monitoring device at a second location, the second monitoring device configured to
        detect and monitor the condition of the aspect of the infrastructure, and
        transmit a data signal including data relating to the condition and a second time stamp; and
    an operations center communicatively coupled to each monitoring device, the operations center configured to
        receive the data from the first and second monitoring devices,
        determine whether the data from the first monitoring device differs from the data from the second monitoring device,
        determine whether a difference in data indicates a problem of contamination within the infrastructure,
        subsequent to the determination of the indication of the problem of contamination, determine an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device,
        determine whether a difference in data indicates a problem of corrosion within the infrastructure, and
        subsequent to the determination of the indication of the problem of corrosion, determining by the operations center whether the data relating to the condition as detected by the first monitoring device and the second monitoring device indicates an amount of corrosion determined to be the problem within the infrastructure, and a level of severity of the corrosion.

15. The system of claim 14, wherein the infrastructure monitoring system disseminates information about the infrastructure from the infrastructure monitoring system including disseminating an indicia of the problem within the infrastructure.

16. The system of claim 14, wherein each monitoring device comprises
    at least one sensor sensing the condition within the infrastructure,
    a data storage device storing data sensed by the at least one sensor,
    a communications device adapted to transmit and receive data, and a first processor communicatively coupled to the at least one sensor, the data storage device, and the communications device.

17. The system of claim 14, wherein the first monitoring device is coupled to a camera.

18. The system of claim 14, wherein subsequent to the determination of the indication of the problem of corrosion, the operations center is further configured to determine a level of severity of the corrosion and determine whether the corrosion is severe enough to warrant fixing based on the level of severity of the corrosion.

* * * * *

UNITED STATES PATENT AND TRADEMARK OFFICE
CERTIFICATE OF CORRECTION

PATENT NO. : 9,934,670 B2  
APPLICATION NO. : 14/928725  
DATED : April 3, 2018  
INVENTOR(S) : Gregory E. Hyland et al.

Page 1 of 1

It is certified that error appears in the above-identified patent and that said Letters Patent is hereby corrected as shown below:

In the Claims

In Column 16, Lines 40-42, in Claim 1, delete "wherein the first aspect, the second aspect, and the third aspect define corrosion, contamination, and another different aspect of the infrastructure." and insert therefor -- "wherein the first aspect, the second aspect, and the third aspect define contamination, corrosion, and another different aspect of the infrastructure." --.

Signed and Sealed this  
Twenty-fifth Day of February, 2020

Andrei Iancu  
*Director of the United States Patent and Trademark Office*